(12) United States Patent
Jain-Pandey et al.

(10) Patent No.: US 7,943,593 B2
(45) Date of Patent: May 17, 2011

(54) COMPOSITIONS COMPRISING INHIBITORS OF IMPDH ENZYME

(75) Inventors: Jugnu Jain-Pandey, Natick, MA (US); Robert J. Fram, Needham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1042 days.

(21) Appl. No.: 10/728,114

(22) Filed: Dec. 4, 2003

(65) Prior Publication Data

US 2005/0059734 A1 Mar. 17, 2005

Related U.S. Application Data

(60) Provisional application No. 60/496,261, filed on Aug. 19, 2003, provisional application No. 60/431,555, filed on Dec. 6, 2002.

(51) Int. Cl.
*A61K 31/70* (2006.01)
*A61K 31/42* (2006.01)
(52) U.S. Cl. .............................. 514/45; 514/48; 514/374
(58) Field of Classification Search .................... 514/45, 514/48, 374
See application file for complete search history.

(56) References Cited

U.S. PATENT DOCUMENTS

| 4,210,745 | A | * | 7/1980 | Montgomery | ............. | 536/27.11 |
| 4,357,324 | A | * | 11/1982 | Montgomery et al. | ......... | 514/45 |
| 6,498,178 | B2 | * | 12/2002 | Stamos et al. | ................. | 514/374 |

FOREIGN PATENT DOCUMENTS

| WO | WO 97/40028 | 10/1997 |
| WO | WO 00/56331 | 9/2000 |

OTHER PUBLICATIONS

Kaufmann, et al. Minireview: Induction of Apoptosis by Cancer Chemotherapy, Exper. Cell. Research, vol. 256, pp. 42-49, (2000).

Jain, et al., "VX-944:. A Specific, Reversible IMPDH Inhibitor with Potent Anti-Proliferative Effects in Human Tumor Cell Lines Derived from Hematological Malignancies," Blood, vol. 100, No. 11, (2002).

Jain, et al., "VX-944, A Novel Inosine Monophosphate Dehydrogenase Inhibitor, Induces Apoptosis and Decreases Proliferation of Lymphoid and Myeloid Cells Derived from Hematological Malignancies", Blood, vol. 102, No. 11, (2003).

\* cited by examiner

*Primary Examiner* — Kevin Weddington
(74) *Attorney, Agent, or Firm* — Michael C. Badia

(57) ABSTRACT

The present invention relates to compositions comprising an apoptosis inducing anti-cancer agent and an IMPDH inhibitor. This invention also relates to methods for inducing apoptosis and for treating tumors and cancers in mammals.

2 Claims, No Drawings

COMPOSITIONS COMPRISING INHIBITORS OF IMPDH ENZYME

CROSS REFERENCE TO RELATED APPLICATIONS

This application claims the benefit under 35 U.S.C. §119(e) of United States provisional application Ser. No. 60/496,261, filed on Aug. 19, 2003 and U.S. provisional application Ser. No. 60/431,555, filed on Dec. 6, 2002 the entire contents of each application being incorporated herein by reference.

TECHNICAL FIELD OF THE INVENTION

The present invention relates to compositions comprising an apoptosis inducing anti-cancer agent and an IMPDH inhibitor. This invention also relates to methods for inducing apoptosis and for treating tumors and cancers.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanine nucleotides. IMPDH catalyzes the NAD-dependent oxidation of inosine-5'-monophosphate (IMP) to xanthosine-5'-monophosphate (XMP) [Jackson R. C. et. al., *Nature*, 256, pp. 331-333, (1975)].

IMPDH is ubiquitous in eukaryotes, bacteria and protozoa [Y. Natsumeda & S. F. Carr, *Ann. N.Y. Acad.*, 696, pp. 88-93 (1993)]. The prokaryotic forms share 30-40% sequence identity with the human enzyme. Two isoforms of human IMPDH, designated type I and type II, have been identified and sequenced [F. R. Collart and E. Huberman, *J. Biol. Chem.*, 263, pp. 15769-15772, (1988); Y. Natsumeda et. al., *J. Biol. Chem.*, 265, pp. 5292-5295, (1990)]. Each is 514 amino acids, and they share 84% sequence identity. Both IMPDH type I and type II form active tetramers in solution, with subunit molecular weights of 56 kDa [Y. Yamada et. al., *Biochemistry*, 27, pp. 2737-2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., *Lancet II*, 1179, (1975) and A. C. Allison et. al., *Ciba Found. Symp.*, 48, 207, (1977)]. Thus, IMPDH is an attractive target for selectively inhibiting the immune system without also inhibiting the proliferation of other cells.

Inhibitors of IMPDH are also known. U.S. Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B and T-cells to mitogen or antigen [A. C. Allison et. al., *Ann. N.Y. Acad. Sci.*, 696, 63, (1993). IMPDH inhibitors of different classes have been described in PCT publications WO 97/40028 and WO 98/40381.

It is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., *Cancer Res.*, 51, pp. 3886-3890, (1991)].

WO 00/56331 discloses IMPDH inhibitors and compositions thereof for treating inter alia tumors and cancers, including compositions comprising an IMPDH inhibitor and an additional anti-cancer agent.

Thus, there remains a need for potent compositions comprising an IMPDH inhibitor with improved pharmacological properties. Such inhibitors would have therapeutic potential as anti-cancer agents.

SUMMARY OF THE INVENTION

The present invention provides pharmaceutical compositions comprising an apoptosis inducing anti-cancer agent, an IMPDH inhibitor, and a pharmaceutically acceptable carrier. The present invention also provides methods of inducing apoptosis in a mammal using the compositions of the present invention. The present invention also provides methods for treating tumors and cancers in a mammal using the compositions of the present invention.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bn | benzyl |
| CDI | carbonyldiimidazole |
| DBU | 1,8-diazabicyclo[5.4.0]undec-7-ene |
| DIEA | diisopropylethylamine |
| DMAP | dimethylaminopyridine |
| DMF | dimethyl formamide |
| DMSO | dimethylsulfoxide |
| DPPA | diphenyl phosphoryl acid |
| EDC | 1-(3-dimethylaminopropyl)-3-ethylcarbodiimide hydrochloride |
| EtOAc | ethyl acetate |
| IPA | isopropyl alcohol |
| MeCN | acetonitrile |
| THF | tetrahydrofuran |
| TEA | triethylamine |
| t-bu | tert-butyl |
| BOC | butyloxycarbonyl |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The terms "halo" or "halogen" refer to a radical of fluorine, chlorine, bromine or iodine.

IMPDH-mediated disease refers to any disease state in which the IMPDH enzyme plays a regulatory role in the metabolic pathway of that disease.

The term "treating" as used herein refers to the alleviation of symptoms of a particular disorder in a patient or the improvement of an ascertainable measurement associated with a particular disorder. As used herein, the term "patient" refers to a mammal, including a human.

According to one embodiment, the invention provides compositions comprising:
1) an apoptosis inducing anti-cancer agent;
2) an IMPDH inhibitor; and
3) a pharmaceutically acceptable carrier.

The term "apoptosis inducing anti-cancer agent," as used herein, means an agent that acts as an anti-metabolite, induces apoptosis, and is useful in treating cancer. See, e.g., "Induction of Apoptosis by Cancer Chemotherapy," Kaufmann, S. H. and Earnshaw, W. C., *Exptal. Cell Res.*, 256, 42-49 (2000). Examples of such anti-metabolites include cytarabine, fludarabine, 5-fluro-2'-deoxyuridine, gemcitabine, hydroxyurea, and methotrexate. See, ibid, Table 1, p. 43.

According to another embodiment, the invention provides compositions comprising:
1) an apoptosis inducing anti-cancer agent;
2) a compound of formula A:

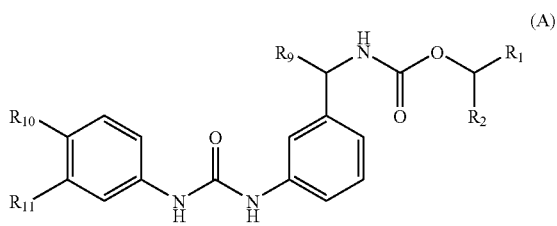

(A)

wherein:
each of $R_1$ and $R_2$ is independently selected from hydrogen; —$CF_3$; —$(C_1-C_6)$-straight or branched alkyl; —$(C_2-C_6)$-straight or branched alkenyl or alkynyl; —$(C_1-C_6)$-straight or branched alkyl-$R_7$; —$[(C_2-C_6)$-straight or branched alkenyl or alkynyl]-$R_7$ or —$R_7$; and wherein at least one of $R_1$ or $R_2$ is —$(C_1-C_6)$-straight or branched alkyl-$R_7$; —$[(C_2-C_6)$-straight or branched alkenyl or alkynyl]-$R_7$ or —$R_7$
wherein up to 4 hydrogen atoms in any of said alkyl, alkenyl or alkynyl are optionally and independently replaced by $R_3$; or
wherein $R_1$ and $R_2$ are alternatively taken together to form tetrahydrofuranyl, wherein when $R_9$ is hydrogen, (R)-methyl, (R)-ethyl or (R)-hydroxymethyl, one hydrogen atom in said tetrahydrofuran is replaced by —$OR_6$ or —$R_7$, and wherein when $R_9$ is (S)-methyl, (S)-ethyl or (S)-hydroxymethyl, one hydrogen atom in said tetrahydrofuran is optionally replaced by —$OR_6$ or —$R_7$;
wherein when $R_9$ is hydrogen, (R)-methyl, (R)-ethyl or (R)-hydroxymethyl and each of $R_1$ and $R_2$ are independently hydrogen, unsubstituted —$(C_1-C_6)$-straight or branched alkyl, or unsubstituted —$(C_2-C_6)$-straight or branched alkenyl or alkynyl, then the portion of the compound represented by —$CH(R_1)R_2$ is a $C_5-C_{12}$ straight or branched alkyl, alkenyl or alkynyl;
each $R_3$ is independently selected from halo, CN, —$OR_4$, or —$N(R_5)_2$;
$R_4$ is selected from hydrogen, —$(C_1-C_6)$-straight or branched alkyl, —$(C_2-C_6)$-straight or branched alkenyl or alkynyl, —$[(C_1-C_6)$-straight or branched alkyl]-$R_7$, —$[(C_2-C_6)$-straight or branched alkenyl or alkynyl]-$R_7$, —$C(O)$—$[(C_1-C_6)$-straight or branched alkyl], —$C(O)$—$[(C_2-C_6)$-straight or branched alkenyl or alkynyl], —$C(O)$—$[(C_1-C_6)$-straight or branched alkyl]-$N(R_8)_2$, —$C(O)$—$[(C_2-C_6)$-straight or branched alkenyl or alkynyl]-$N(R_8)_2$, —$P(O)(OR_8)_2$, —$P(O)(OR_8)(R_8)$, —$C(O)$—$R_7$, —$[(C_1-C_6)$-straight or branched alkyl]-CN, —$S(O)_2N(R_5)_2$ or —$[(C_2-C_6)$-straight or branched alkenyl or alkynyl]-CN;

each $R_5$ is independently selected from hydrogen, —$(C_1-C_6)$-straight or branched alkyl, —$(C_2-C_6)$-straight or branched alkenyl or alkynyl, —$[(C_1-C_6)$-straight or branched alkyl]-$R_7$, —$[(C_2-C_6)$-straight or branched alkenyl or alkynyl]-$R_7$, —$[(C_1-C_6)$-straight alkyl]-CN, —$[(C_2-C_6)$-straight or branched alkenyl or alkynyl]-CN, —$[(C_1-C_6)$-straight or branched alkyl]-$OR_4$, —$[(C_2-C_6)$-straight or branched alkenyl or alkynyl]-$OR_4$, —$C(O)$—$(C_1-C_6)$-straight or branched alkyl, —$C(O)$—$[(C_2-C_6)$-straight or branched alkenyl or alkynyl], —$C(O)$—$R_7$, —$C(O)O$—$R_7$, —$C(O)O$—$(C_1-C_6)$-straight or branched alkyl, —$C(O)O$—$[(C_2-C_6)$-straight or branched alkenyl or alkynyl], —$S(O)_2$—$(C_1-C_6)$-straight or branched alkyl, or —$S(O)_2$—$R_7$; or two $R_5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or $S(O)_2$;
$R_6$ is selected from —$C(O)$—$CH_3$, —$CH_2$—$C(O)$—OH, —$CH_2$—$C(O)$—O-tBu, —$CH_2$—CN, or —$CH_2$—C≡CH;
each $R_7$ is a monocyclic or bicyclic ring system wherein in said ring system:
i. each ring comprises 3 to 7 ring atoms independently selected from C, N, O or S;
ii. no more than 4 ring atoms are selected from N, O or S;
iii. any $CH_2$ is optionally replaced with C(O);
iv. any S is optionally replaced with S(O) or $S(O)_2$;
each $R_8$ is independently selected from hydrogen or —$[C_1-C_4]$-straight or branched alkyl;
wherein in any ring system in said compound up to 3 hydrogen atoms bound to the ring atoms are optionally and independently replaced with halo, hydroxy, nitro, cyano, amino, $(C_1-C_4)$-straight or branched alkyl; O—$(C_1-C_4)$-straight or branched alkyl, $(C_2-C_4)$-straight or branched alkenyl or alkynyl, or O—$(C_2-C_4)$-straight or branched alkenyl or alkynyl; and
wherein any ring system is optionally benzofused;
$R_9$ is selected from hydrogen, (R)-methyl, (S)-methyl, (R)-ethyl, (S)-ethyl, (R)-hydroxymethyl or (S)-hydroxymethyl;
$R_{10}$ is selected from —C≡N or 5-oxazolyl; and
$R_{11}$ is selected from halo, —O—$(C_1-C_3)$ straight alkyl, or —O—$(C_2-C_3)$ straight alkenyl or alkynyl; and
3) a pharmaceutically acceptable carrier.

Also within the scope of formula (A) are prodrugs, which are formed by esterifying either or both of $R_1$ or $R_2$. Examples of such prodrugs are compounds 143 to 156 in Table 1, set forth below.

According to a preferred embodiment, the apoptosis inducing anti-cancer agent is cytarabine, fludarabine, 5-fluro-2'-deoxyuridine, or gemcitabine. More preferably, it is cytarabine, fludarabine, or 5-fluro-2'-deoxyuridine. Even more preferably, it is fludarabine or cytarabine. Most preferably, it is fludarabine.

According to another preferred embodiment, the apoptosis inducing anti-cancer agent is hydroxyurea or methotrexate. More preferably it is hydroxyurea. According to an alternate more preferred embodiment, it is methotrexate.

The term "monocyclic ring system", as used herein, includes saturated, partially unsaturated and fully unsaturated ring structures. The term "bicyclic ring system", as used herein, includes systems wherein each ring is independently saturated, partially unsaturated and fully unsaturated. Examples of monocyclic and bicyclic ring systems useful in the compounds of this invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyan, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine. Additional monocyclic and bicyclic structures falling within the above description may be found in A. R. Katritzky, and C. W. Rees, eds. "*Comprehensive Heterocyclic Chemistry: Structure, Reactions, Synthesis and Use of Heterocyclic Compounds, Vol. 1-8,*" Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system). The term "ring atom" does not include hydrogen.

The terms "—[(C$_1$-C$_6$)-straight or branched alkyl]-X" and "—[(C$_2$-C$_6$)-straight or branched alkenyl or alkynyl]-X", wherein X is anything indicated as being bound to the alkyl, alkenyl or alkynyl, denotes that one or more X groups may be attached to the alkyl, alkenyl or alkynyl chain at any termini.

The present invention is a selection over International PCT Application WO 00/56331 (hereinafter "WO 00/56331"), entitled "Inhibitors of IMPDH Enzyme", the disclosure of which is incorporated herein by reference. Applicants have discovered that when an IMPDH inhibitor, such as those described in WO 00/56331, is combined with an apoptosis inducing anti-cancer agent, such as fludarabine, the resulting composition exhibits strong synergistic effect in inducing apoptosis. This strong synergy renders the compositions of the present invention therapeutically useful in inducing apoptosis and in treating tumors and cancers in mammals.

According to one preferred embodiment, the composition of the present invention comprises a compound of formula (I):

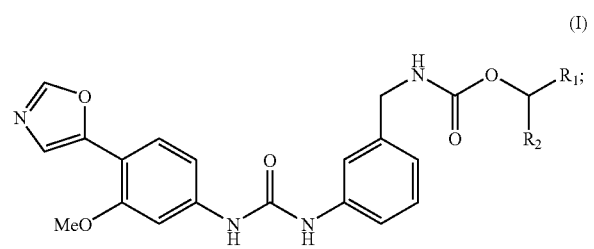

(I)

wherein R$_1$ and R$_2$ are as defined above.

According to another preferred embodiment, the composition of the present invention comprises a compound of formula (IA):

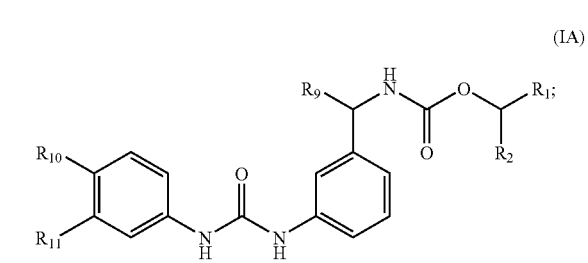

(IA)

wherein R$_9$ is selected from (R)-methyl, (S)-methyl, (R)-ethyl, (S)-ethyl, (R)-hydroxymethyl or (S)-hydroxymethyl; and R$_1$, R$_2$, R$_{10}$ and R$_{11}$ are as defined above.

According to a more preferred embodiment of formula IA, R$_9$ is selected from (S)-methyl, (S)-ethyl, or (S)-hydroxymethyl methyl. Most preferably, R$_9$ is (S)-methyl. Compounds wherein R$_9$ is selected from (S)-methyl, (S)-ethyl, or (S)-hydroxymethyl methyl and wherein the portion of the compound represented by —CH(R$_1$)R$_2$ is a C$_1$-C$_4$ straight or branched alkyl, or a C$_2$-C$_4$ straight or branched alkenyl or alkynyl fall within the genus of compounds described in WO 97/40028. However, applicants have discovered that the presence of an (S) oriented moiety at R$_9$ imparts surprising and unexpectedly increased IMPDH inhibitory activity.

According to another preferred embodiment of formula IA, R$_{11}$ is selected from O-methyl, O-ethyl or O-isopropyl.

According to a more preferred embodiment of formulae (I) and (IA), at least one of R$_1$ or R$_2$ is selected from hydrogen, methyl, ethyl, n-propyl, isopropyl, n-butyl, t-butyl, n-pentyl, phenyl, pyridyl, —CH$_2$OCH$_3$, —CH$_2$CN, —CH$_2$OCH$_2$CH$_2$CN, —CH$_2$C(CH$_3$)$_2$CH$_2$CH$_2$CN, —CH$_2$C(CH$_2$CH$_3$)$_2$CH$_2$CH$_2$CN, —CH$_2$CH$_2$CN, —CH$_2$N(CH$_2$CH$_2$CN)$_2$, —CH$_2$N(CH$_3$)CH$_2$CH$_2$CN, —CH(NH$_2$)CH$_2$CN, —CH$_2$Cl, —CH$_2$OH, —CH$_2$CH$_2$OH, —CH$_2$CH$_2$OH, —CH$_2$CH$_2$CH$_2$OH, —CH$_2$CH$_2$OC(O)CH$_3$, —CH$_2$CH$_2$OC(O)CH$_2$NH$_2$, —CH$_2$CH$_2$NHCH$_3$, —CH$_2$CH$_2$N(CH$_3$)$_2$, —CH$_2$CH$_2$N(CH$_2$CH$_3$)$_2$, —CH$_2$N(CH$_2$CH$_3$)$_2$, —CH$_2$CH$_2$CH$_2$N(CH$_3$)$_2$, —CH$_2$CH$_2$CH$_2$N$^+$(CH$_3$)$_3$, —CH$_2$OCH$_2$CH(CH$_3$)$_2$, —CH$_2$CH$_2$N(CH$_3$)C(O)OC(CH$_3$)$_3$, —CH$_2$N(CH$_2$CH$_2$CN)CH$_2$CH(CH$_3$)$_2$, —CH(CH$_2$CN)N(CH$_3$)$_2$, —CH$_2$CH(CH$_2$CN)NHC(O)OC(CH$_3$)$_3$,

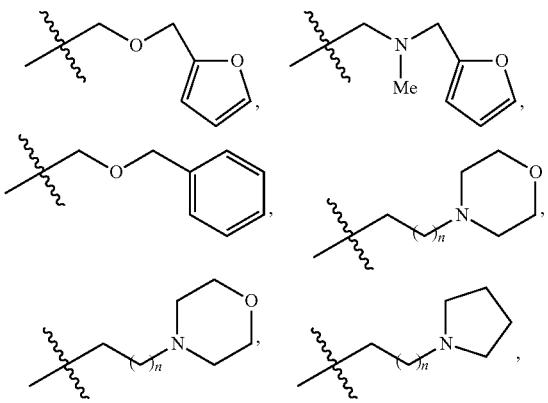

-continued

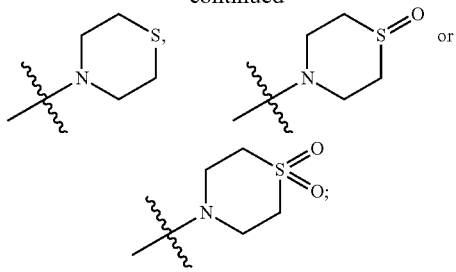

wherein n is 0 or 1.

According to an even more preferred embodiment of formula IA, one of $R_1$ or $R_2$ is selected from hydrogen, ethyl or phenyl; and the other of $R_1$ or $R_2$ is selected from —$CH_2OH$, —$CH_2CN$, —$CH_2CH_2CN$ or $CH_2N(CH_2CH_3)_2$; or $R_1$ and $R_2$ are taken together to form a 3-tetrahydrofuranyl moiety.

According to an alternate preferred embodiment of formula I, $R_1$ and $R_2$ are taken together to form a 3-tetrahydrofuranyl moiety that is substituted by —$OR_6$.

According to another preferred embodiment, the compound of formula A is selected from any of those set forth in Table 1, below.

TABLE 1

Compounds.

1 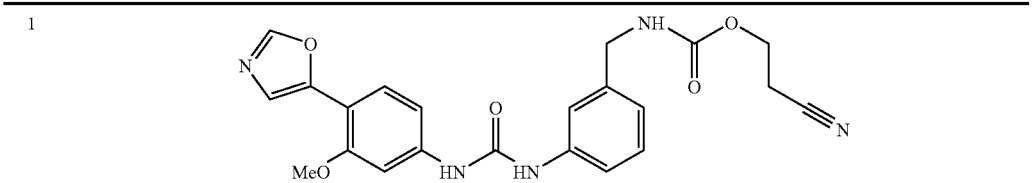

2 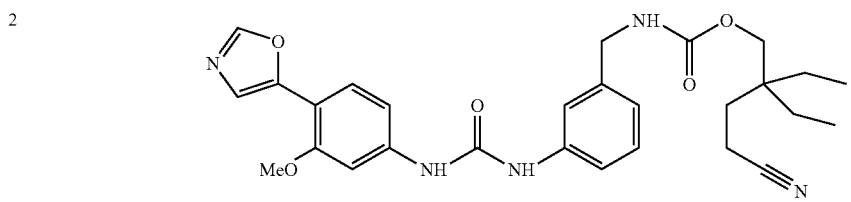

3 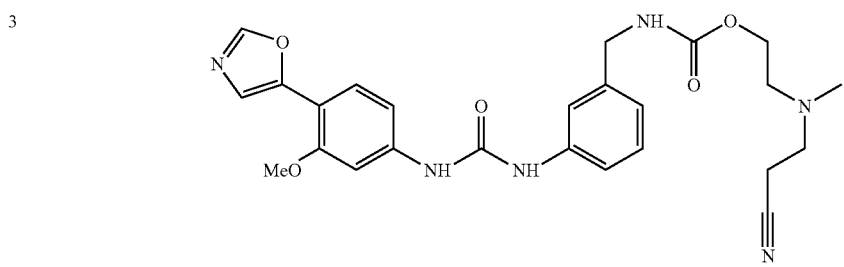

4 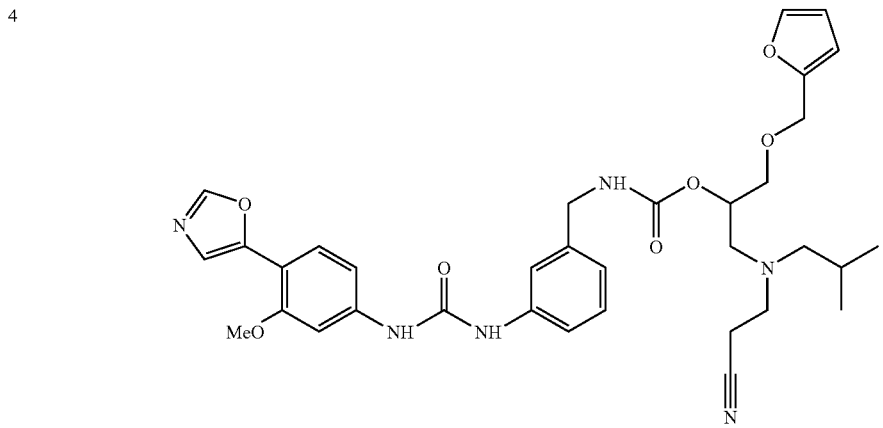

TABLE 1-continued

Compounds.

| | |
|---|---|
| 5 | (structure) |
| 6 | Chiral (structure) |
| 7 | (structure) |
| 8 | (structure) |
| 9 | Chiral (structure) |
| 10 | Chiral (structure) |

TABLE 1-continued

Compounds.

| 11 | (Chiral structure) |
| 12 | (structure) |
| 13 | (structure) |
| 14 | (structure) |
| 15 | (Chiral structure) |
| 16 | (Chiral structure) |
| 17 | (Chiral structure) |

TABLE 1-continued

Compounds.

| # | | |
|---|---|---|
| 18 | Chiral | (structure) |
| 19 | Chiral | (structure) |
| 20 | Chiral | (structure) |
| 21 | Chiral | (structure) |
| 22 | | (structure) |
| 23 | Chiral | (structure) |
| 24 | | (structure) |

TABLE 1-continued

Compounds.

| 25 | (structure of compound 25, chiral) |
| 26 | (structure of compound 26) |
| 27 | (structure of compound 27) |
| 28 | (structure of compound 28, chiral) |
| 29 | (structure of compound 29, chiral) |
| 30 | (structure of compound 30) |
| 31 | (structure of compound 31) |

TABLE 1-continued
Compounds.
32 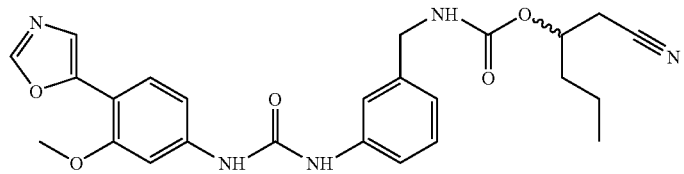
33 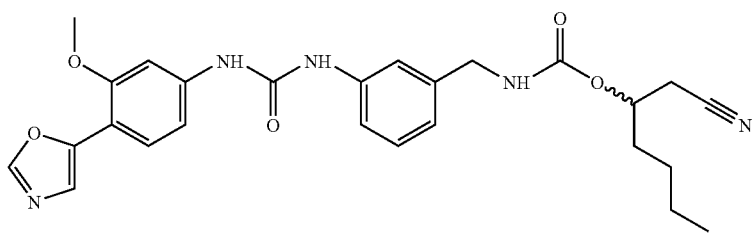
34 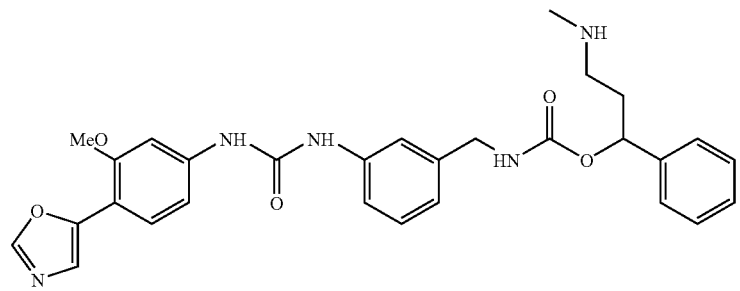
35 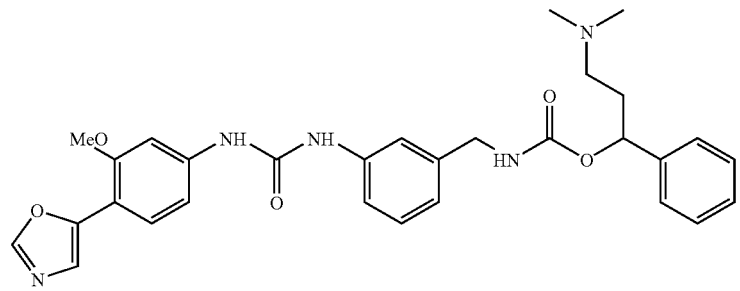
36 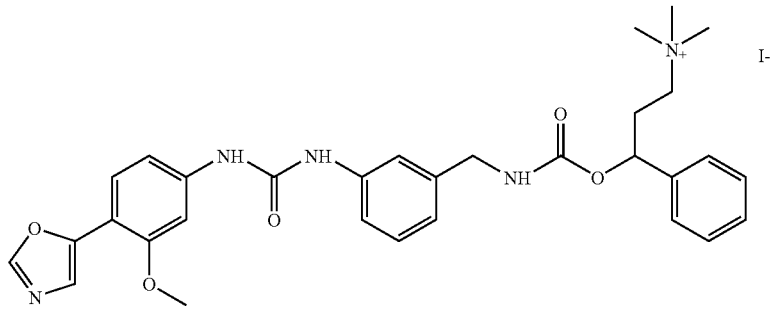
37 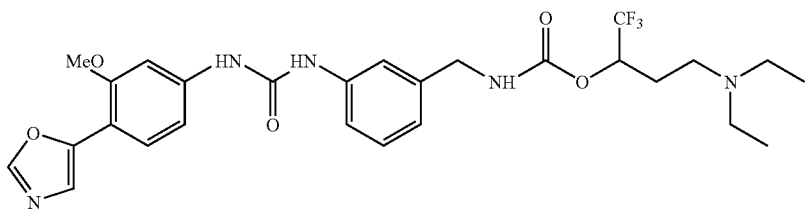

TABLE 1-continued
Compounds.
38
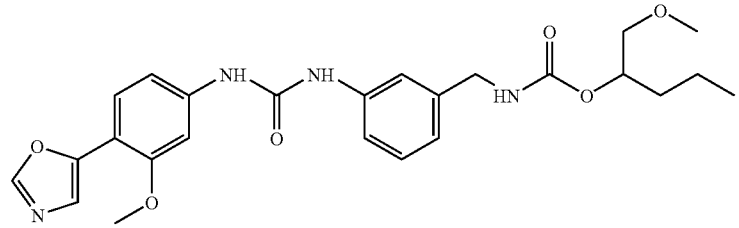
39  Chiral
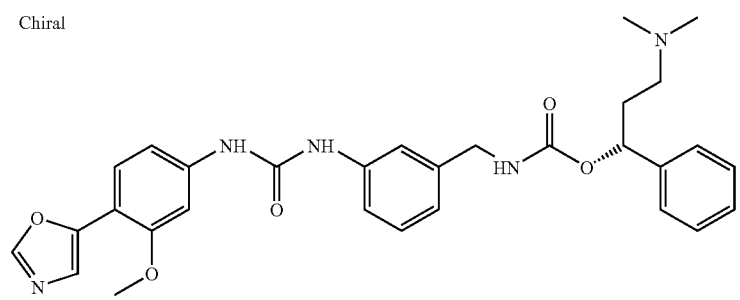
40
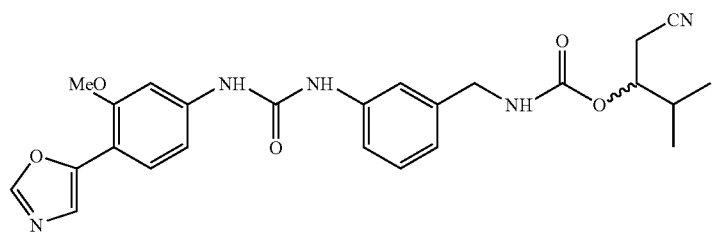
41
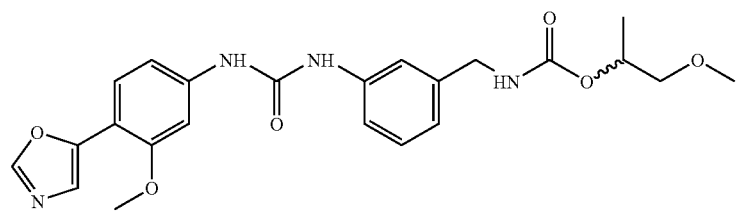
42
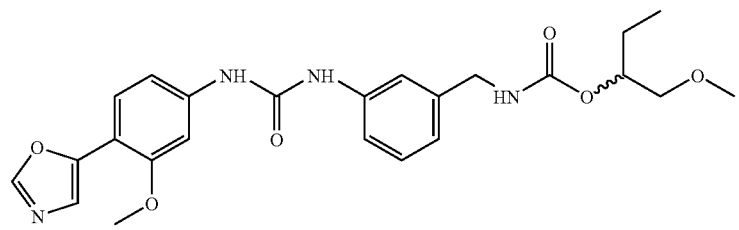
43
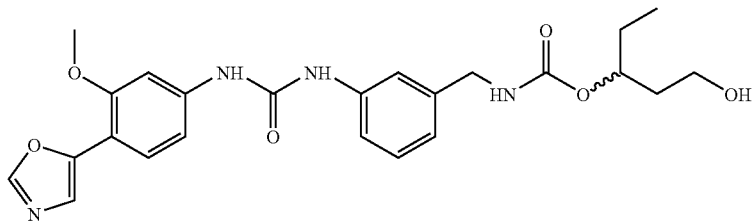

TABLE 1-continued
Compounds.
44
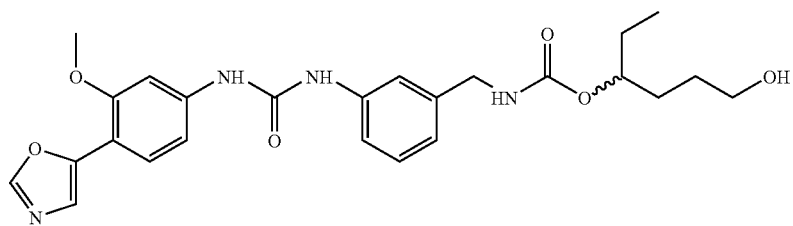
45
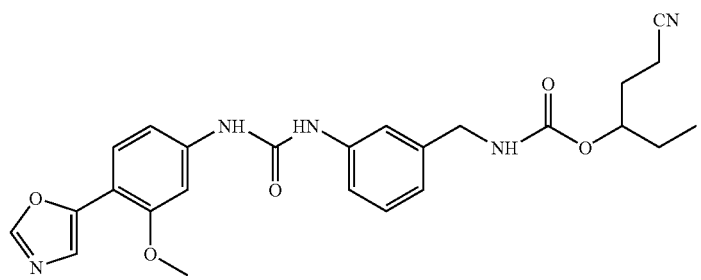
46
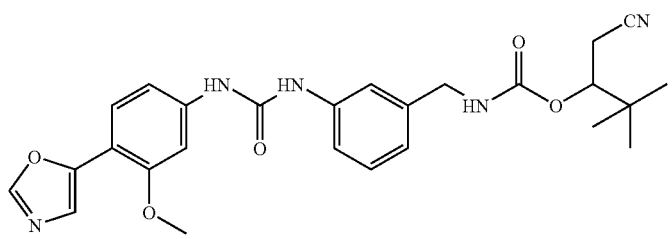
47  Chiral
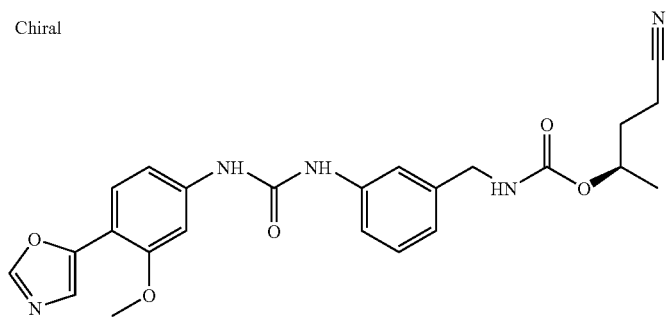
48
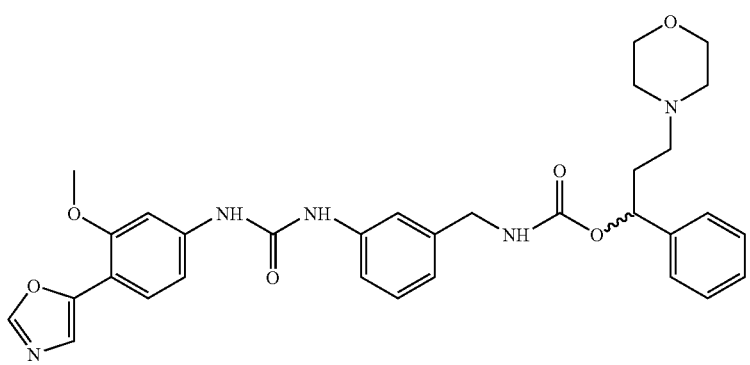

TABLE 1-continued
Compounds.
49
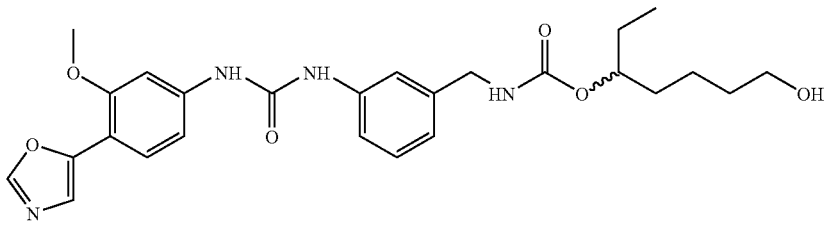
50
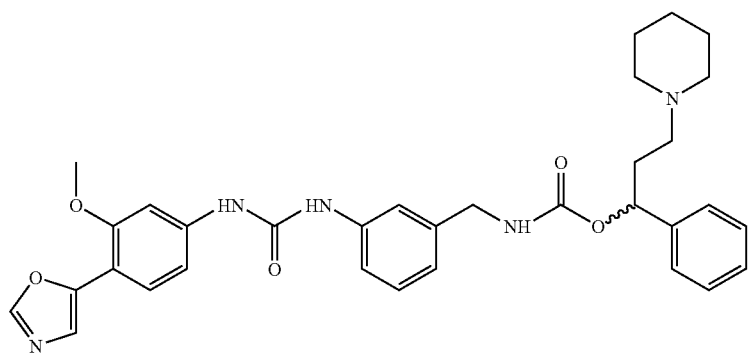
51  Chiral
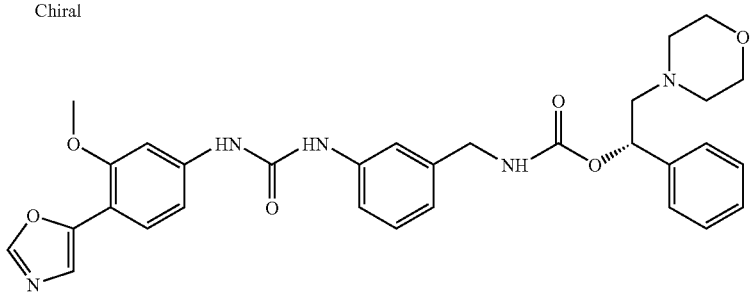
52  Chiral
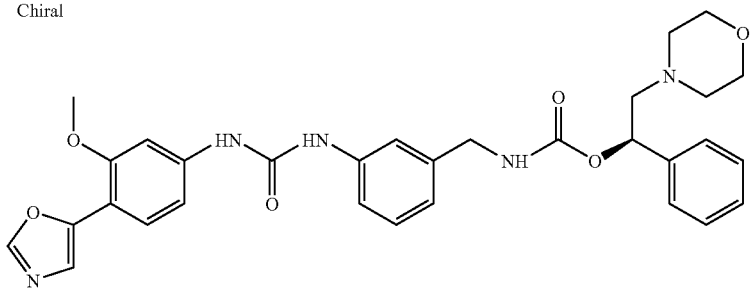
53
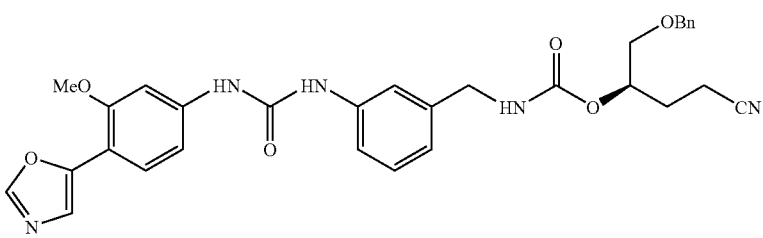

TABLE 1-continued
Compounds.
54
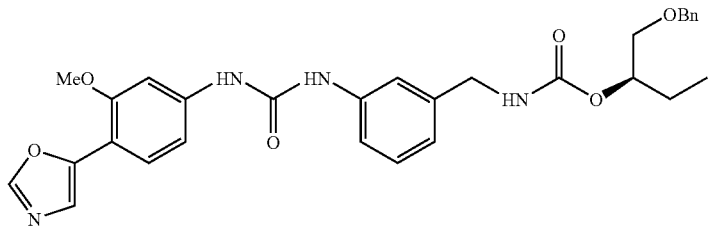
55
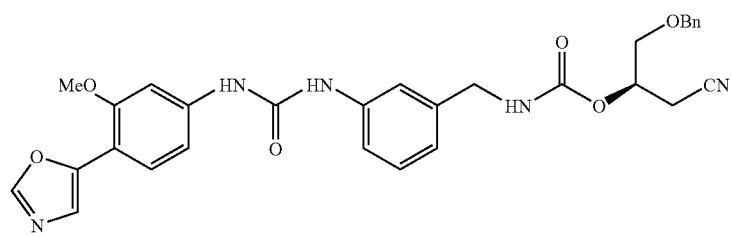
56
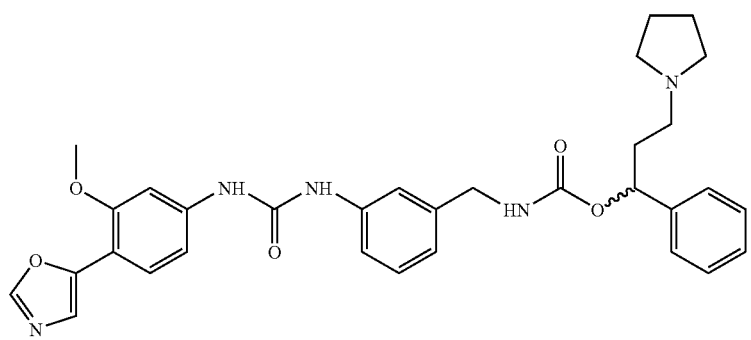
57
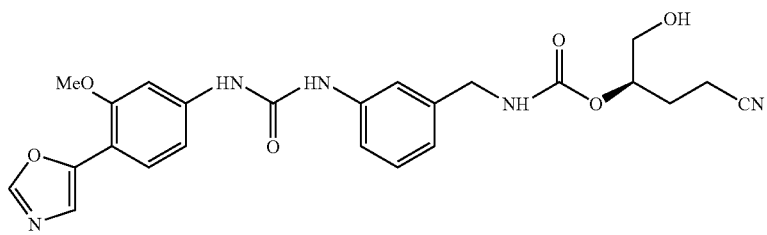
58
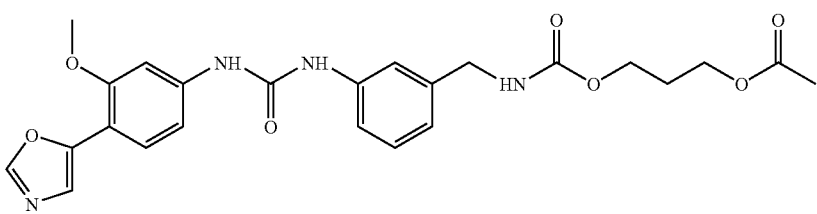
59
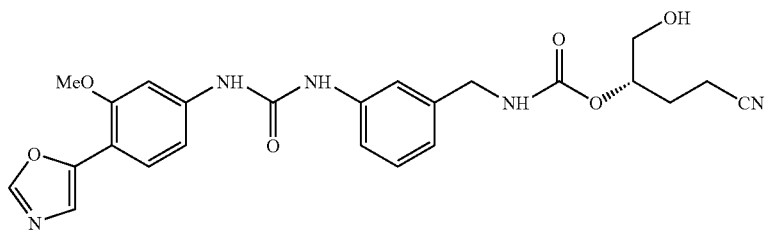

TABLE 1-continued
Compounds.
| | | |
|---|---|---|
| 60 | Chiral | 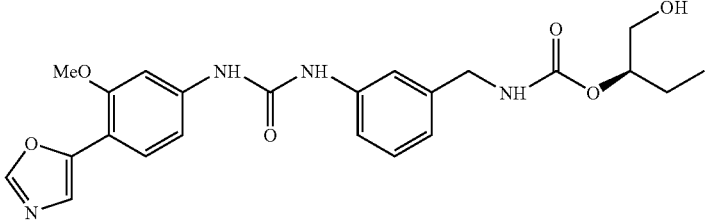 |
| 61 | Chiral | 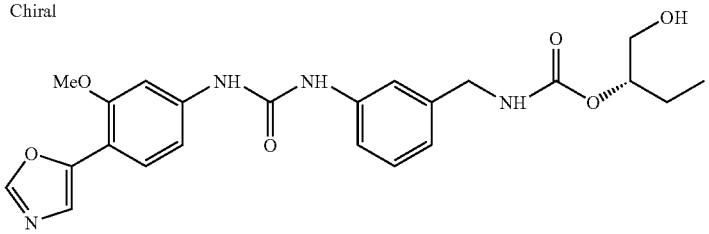 |
| 62 | Chiral | 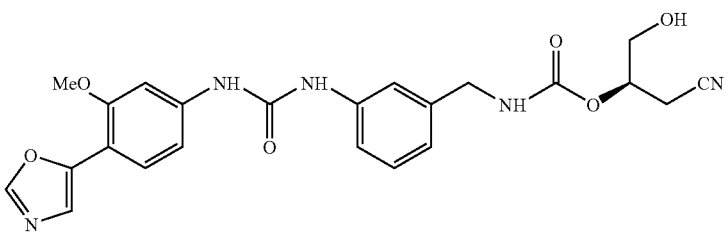 |
| 63 | Chiral | 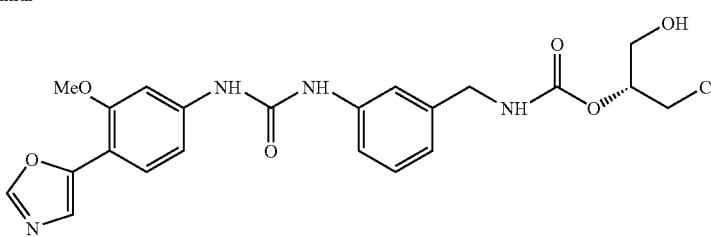 |
| 64 | | 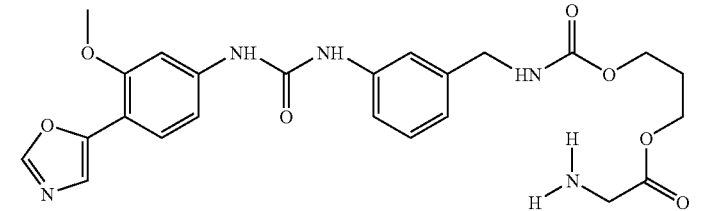 |

TABLE 1-continued
Compounds.
65
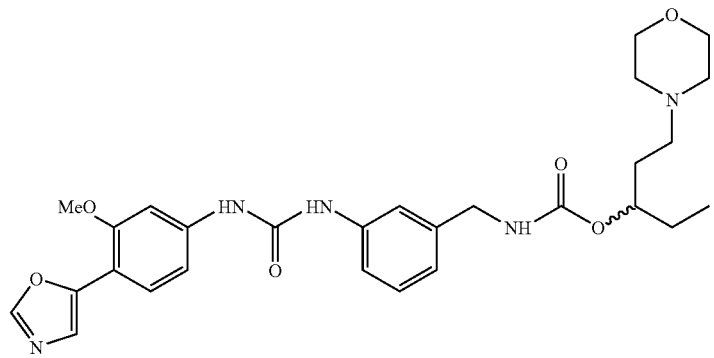
66  Chiral
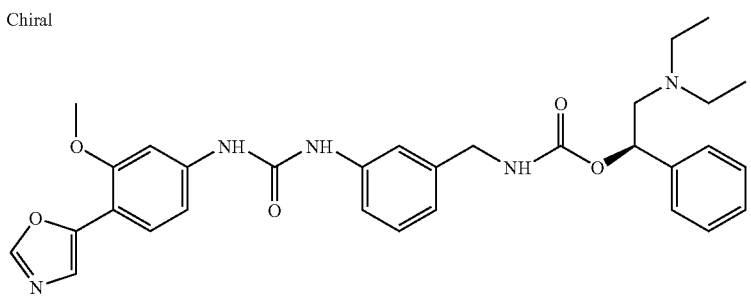
67  Chiral
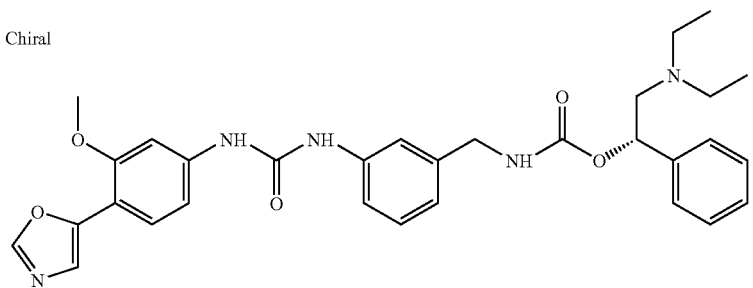
68  Chiral
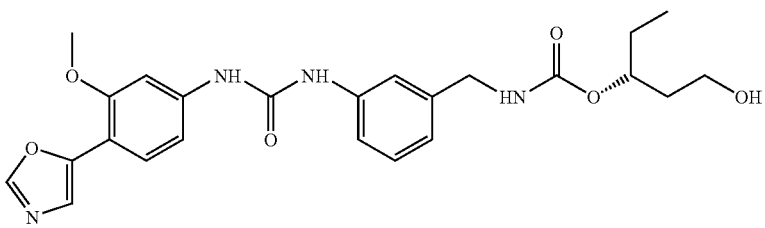
69  Chiral
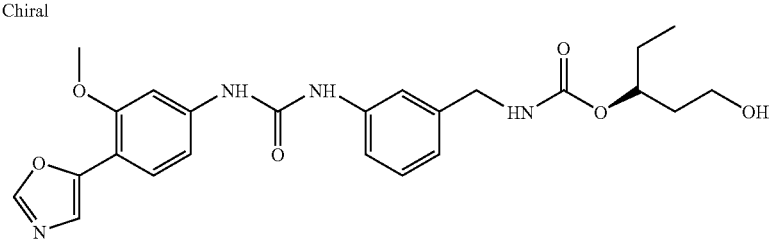

TABLE 1-continued
Compounds.
70 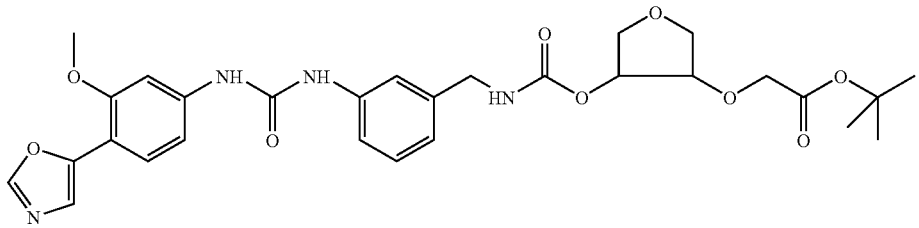
71 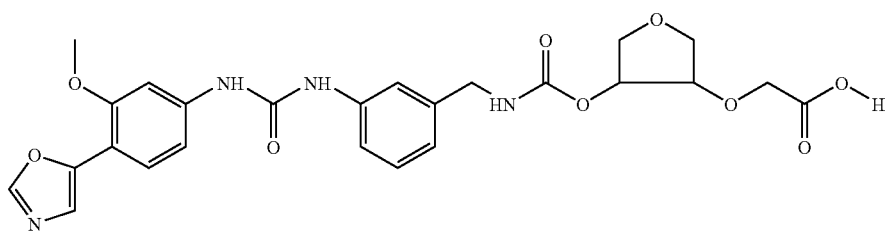
72 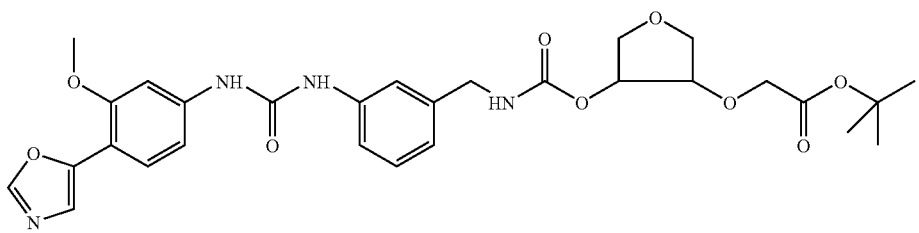
73 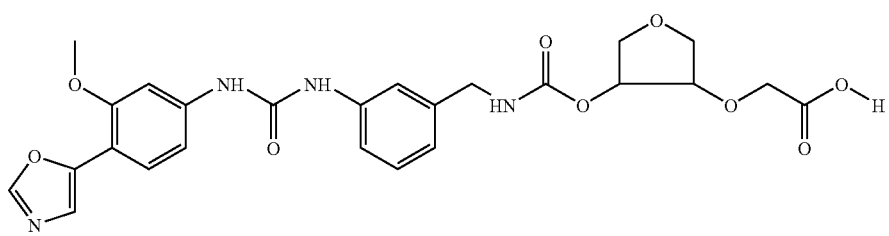
74 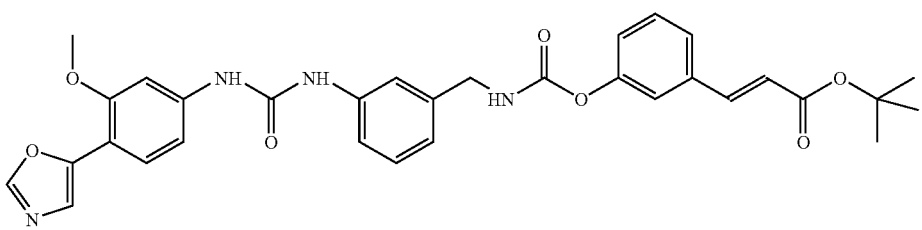
75 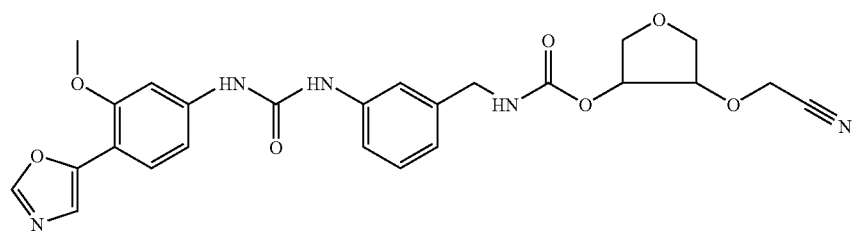

TABLE 1-continued
Compounds.
76
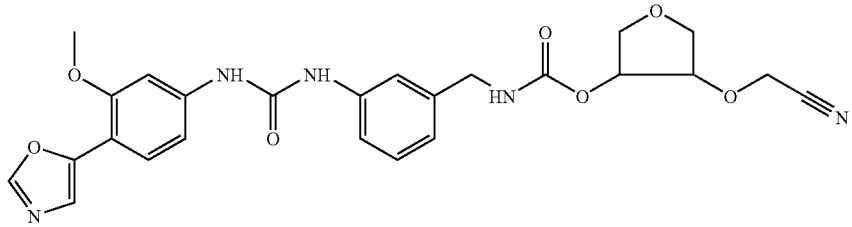
77  Chiral
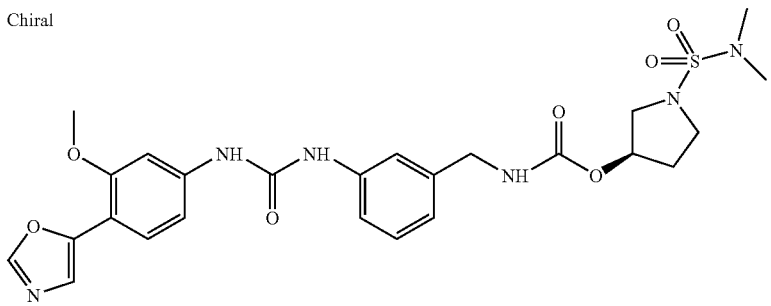
78  Chiral
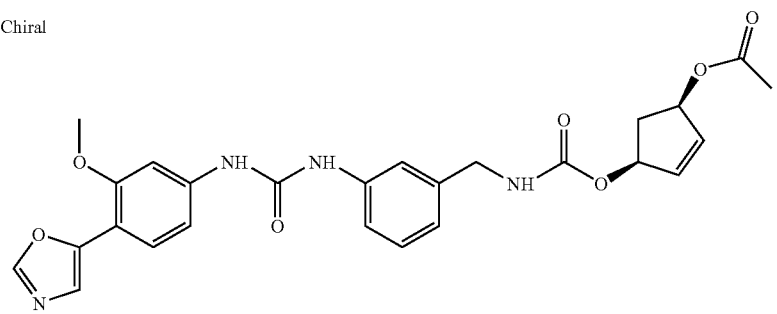
79  Chiral
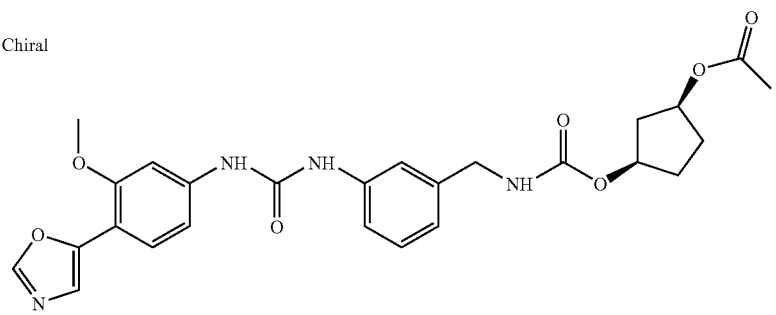
80
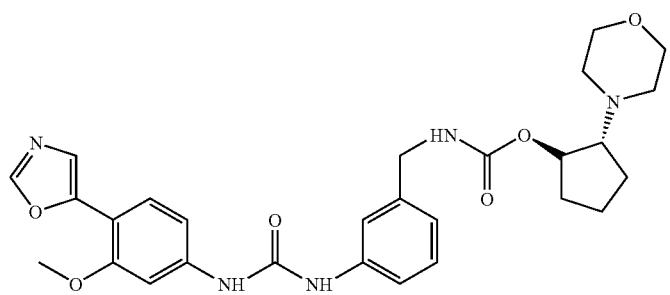

TABLE 1-continued
Compounds.
81 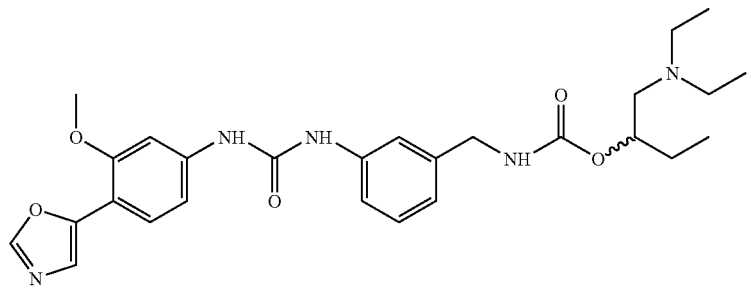
82 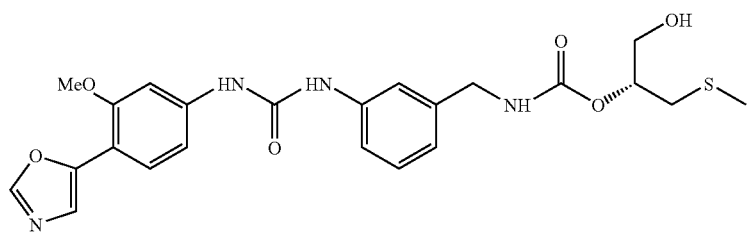
83 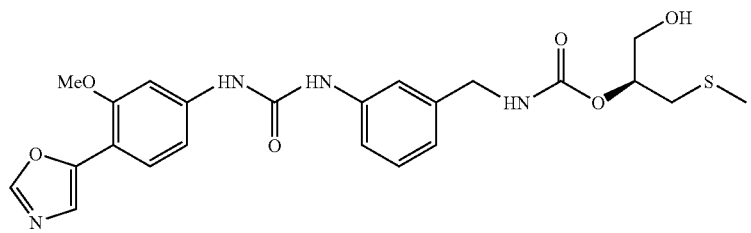
84 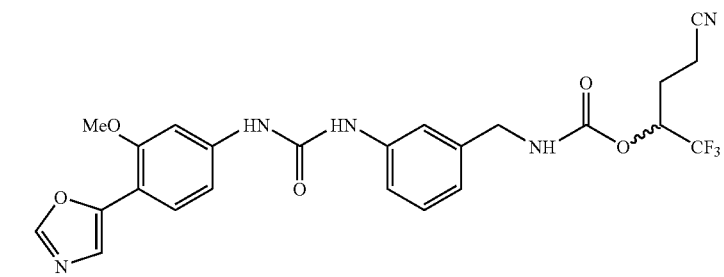
85 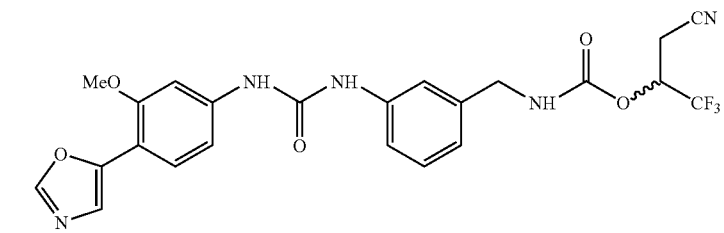
86 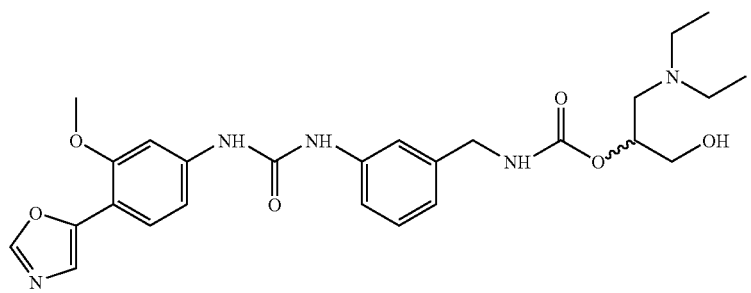

TABLE 1-continued
Compounds.
| 87 | Chiral 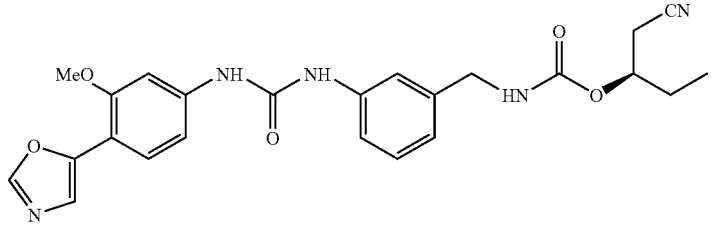 |
| 88 | 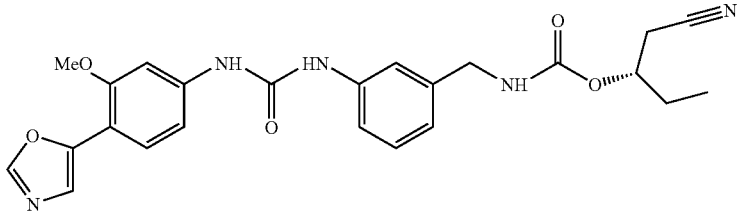 |
| 89 | Chiral 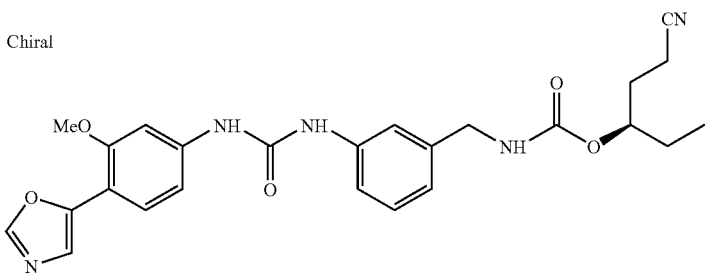 |
| 90 | 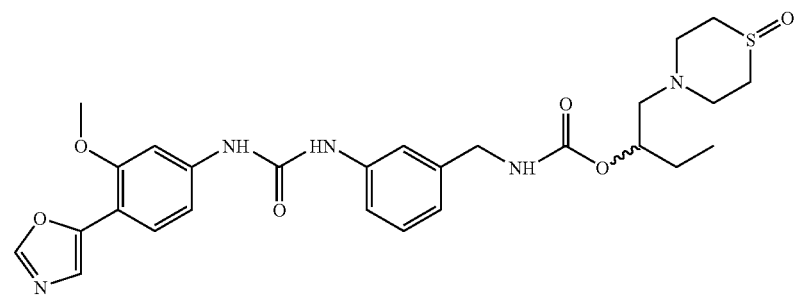 |
| 91 | 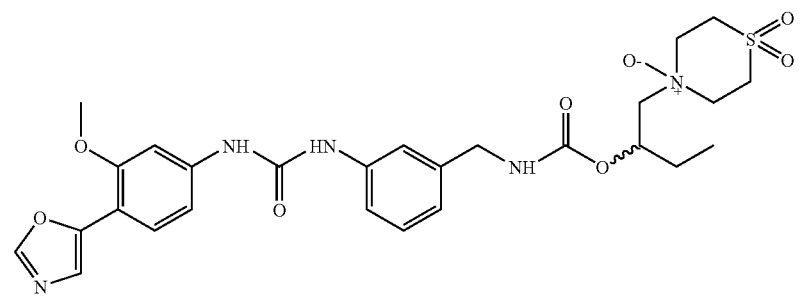 |

TABLE 1-continued
Compounds.
92 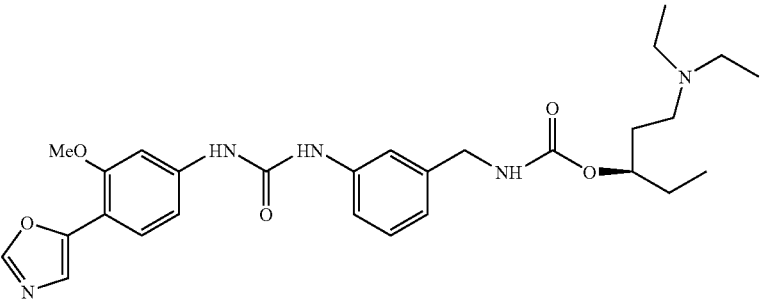
93 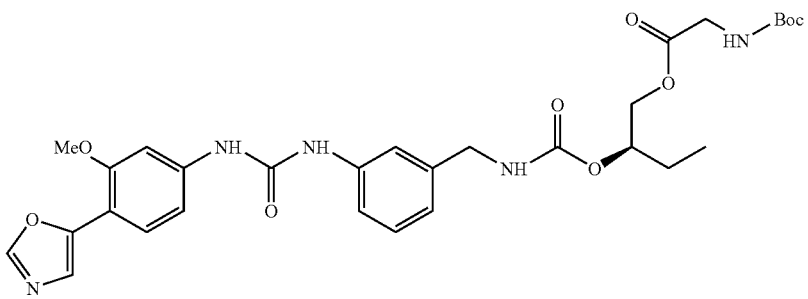
94 Chiral 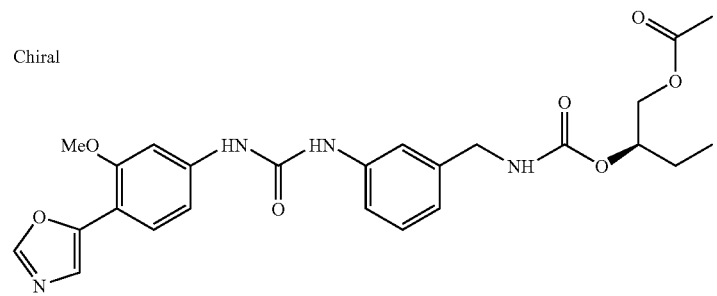
95 Chiral 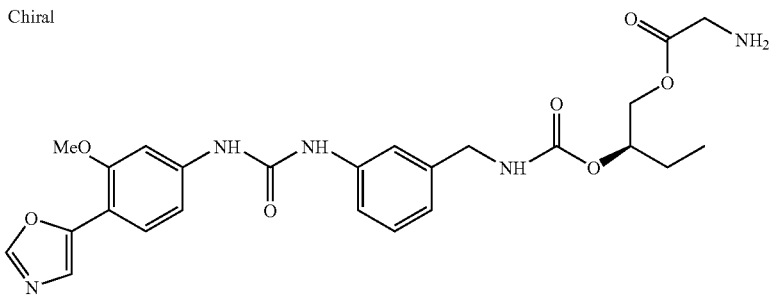
96 Chiral 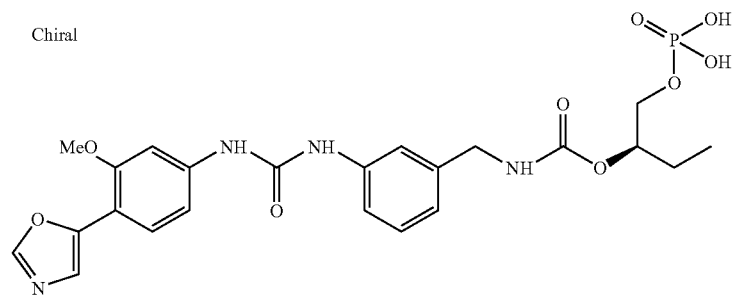

TABLE 1-continued
Compounds.
97 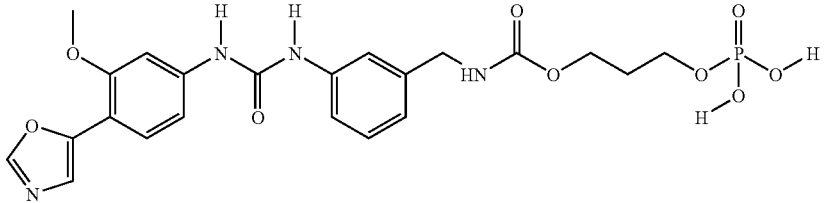
98 Chiral 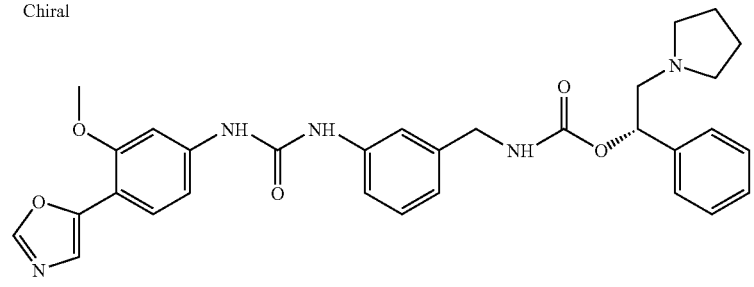
99 Chiral 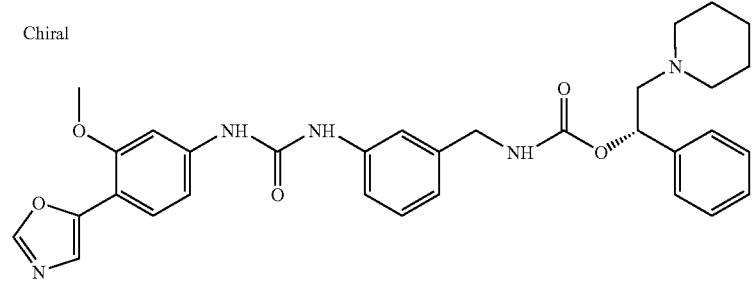
100 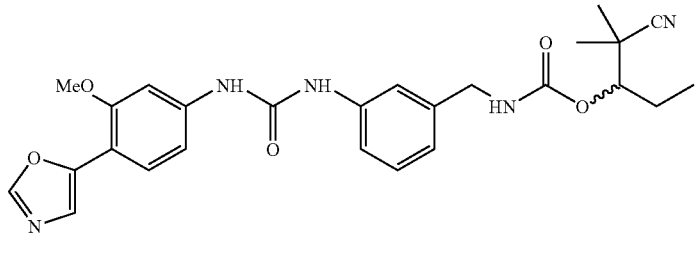
101 Chiral 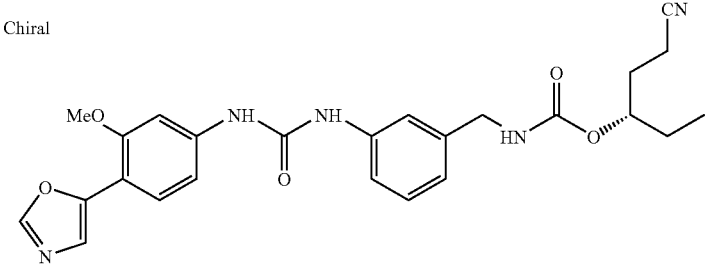

TABLE 1-continued
Compounds.
102 Chiral
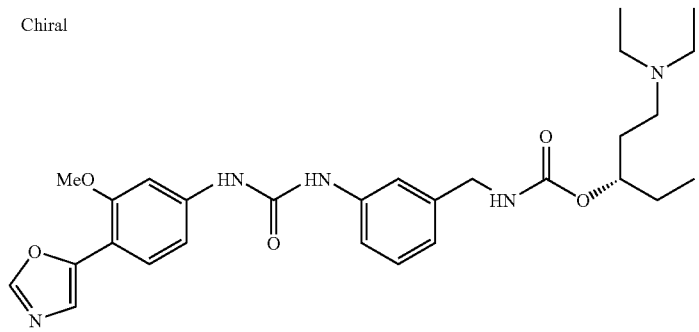
103
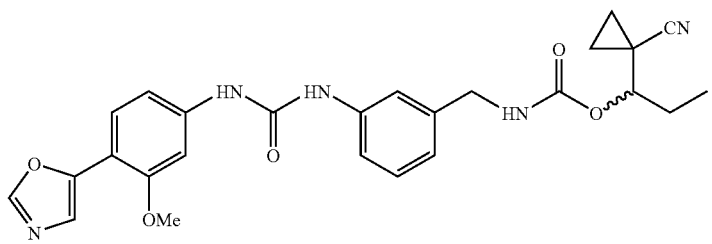
104
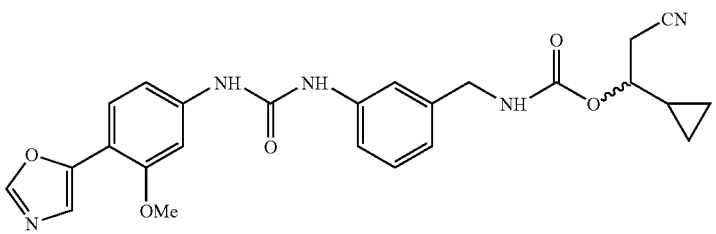
105 Chiral
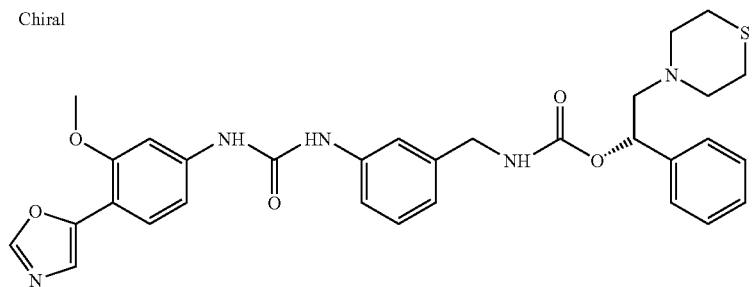
106 Chiral
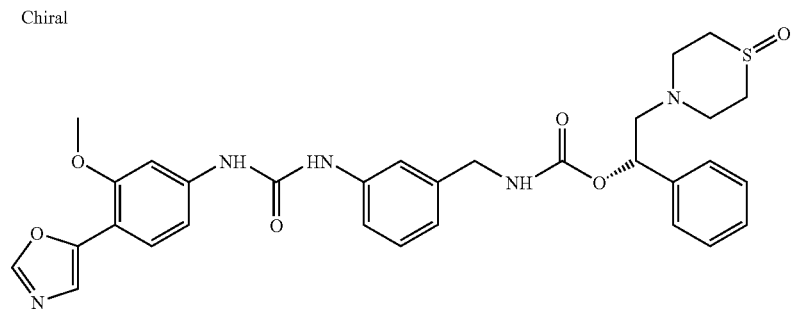

US 7,943,593 B2
45
46
TABLE 1-continued
Compounds.
107 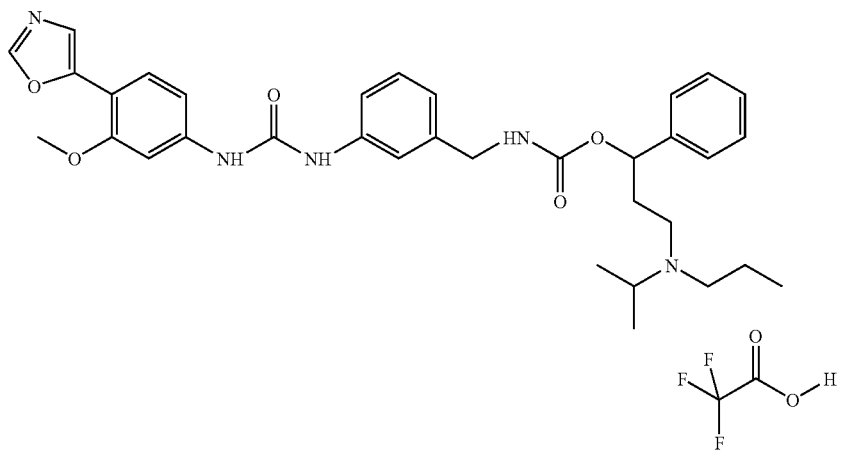
108 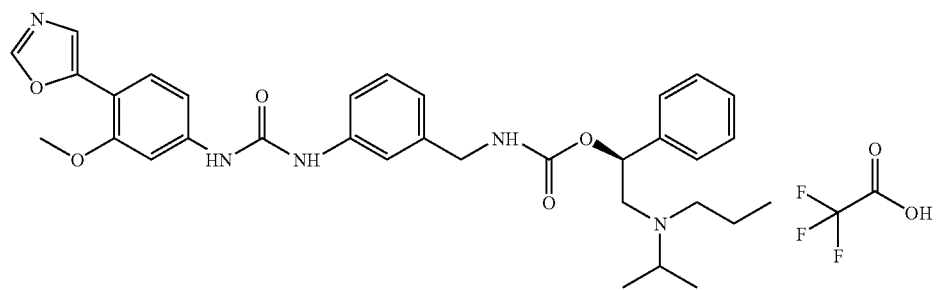
109 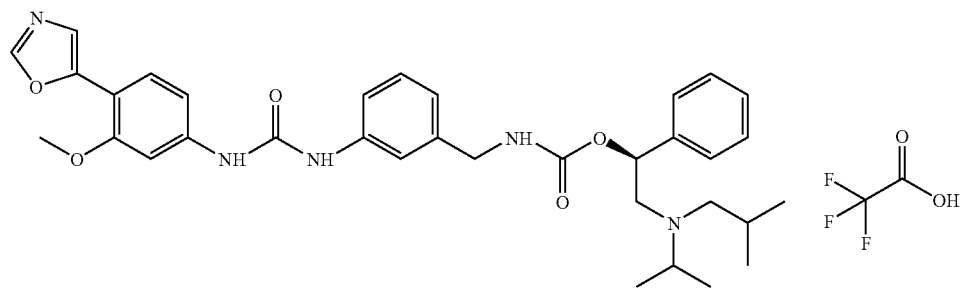
110 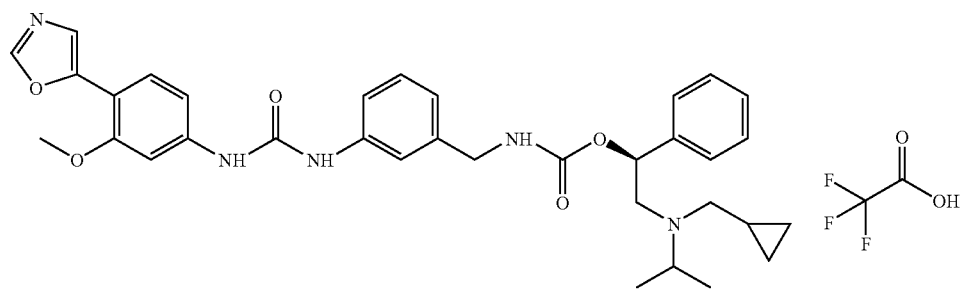

TABLE 1-continued
Compounds.
111
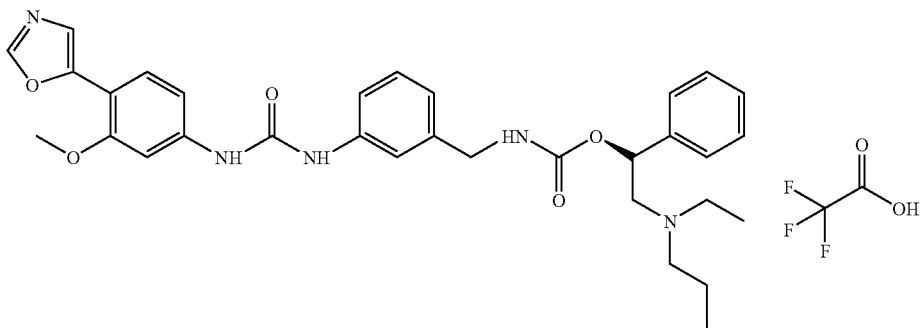
112
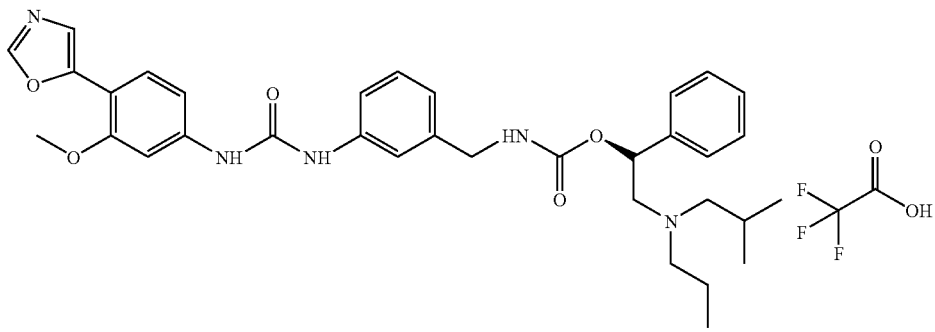
113
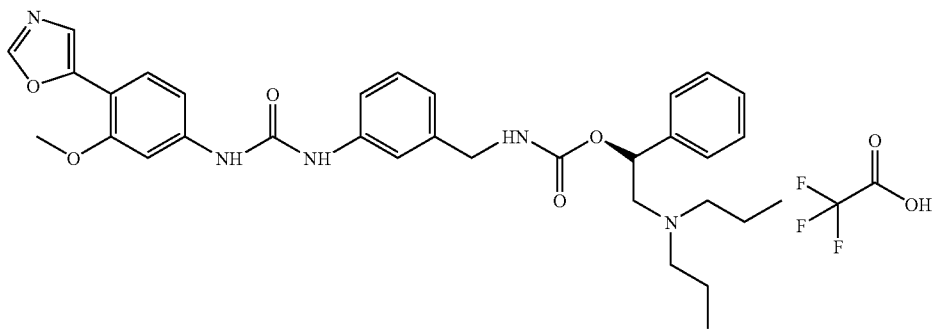
114
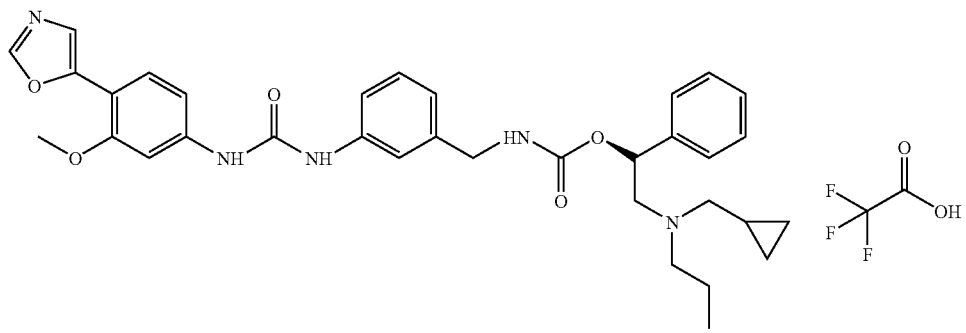

TABLE 1-continued
Compounds.
115
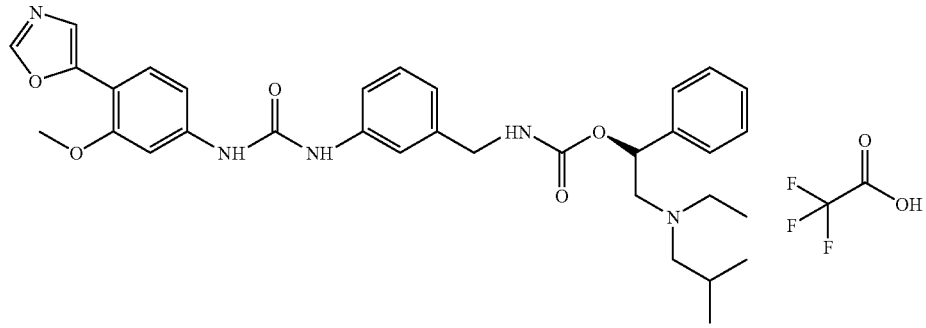
116
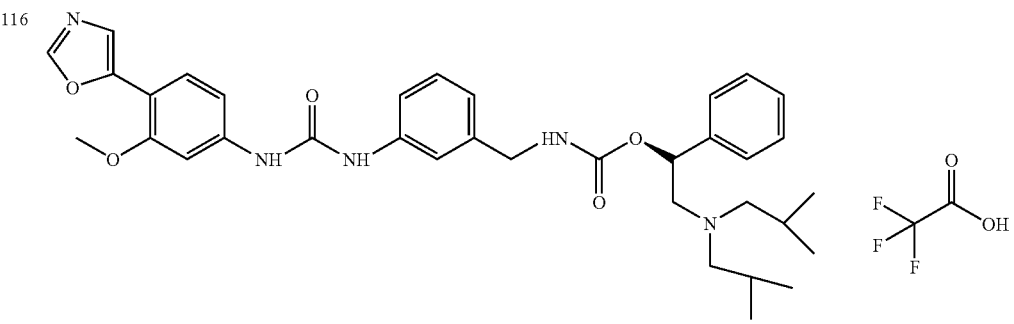
117
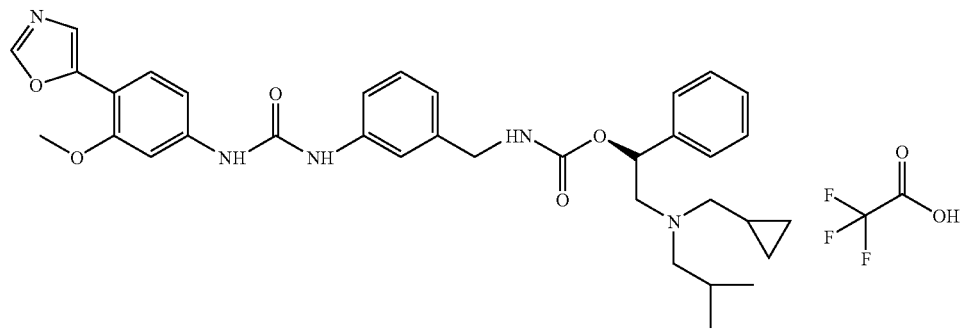
118
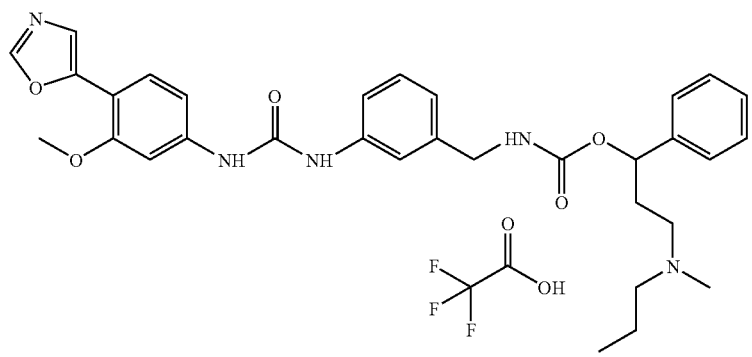

TABLE 1-continued
Compounds.
119 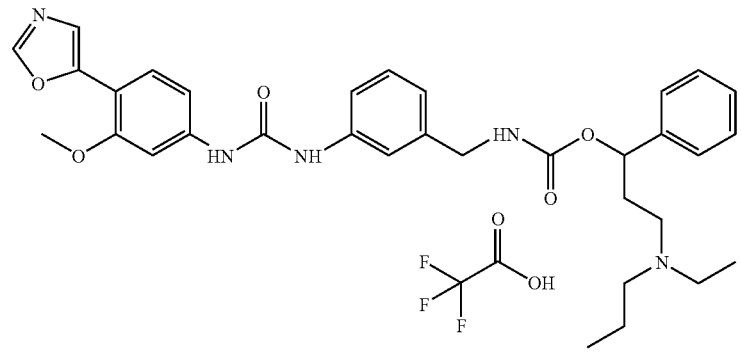
120 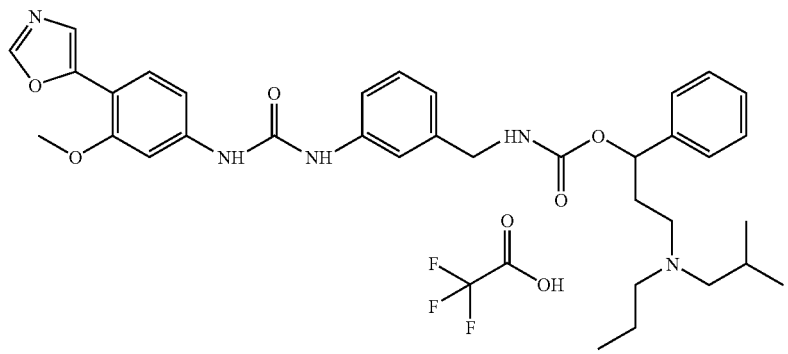
121 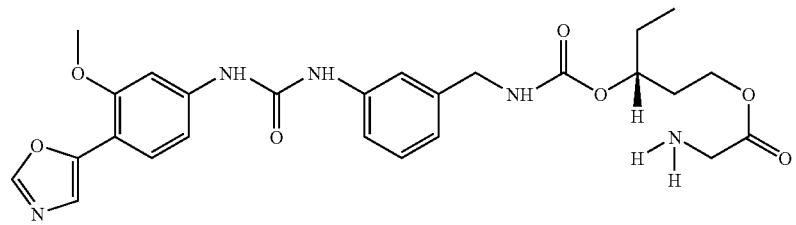
122 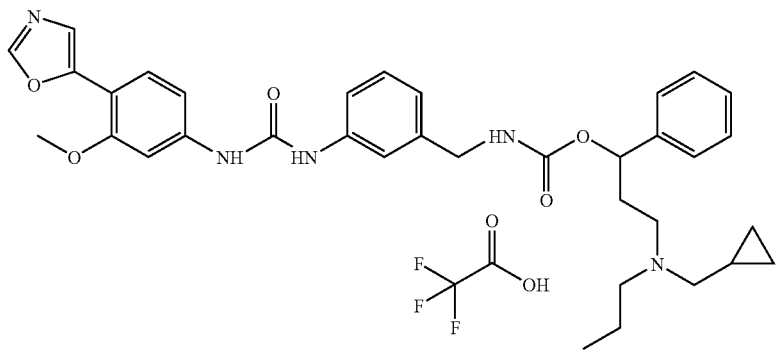

TABLE 1-continued
Compounds.
123 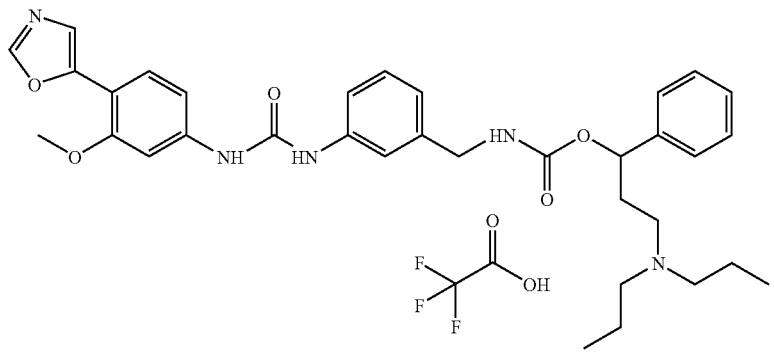
124 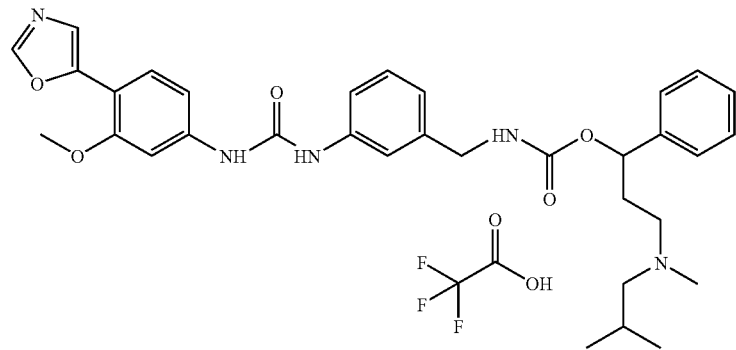
125 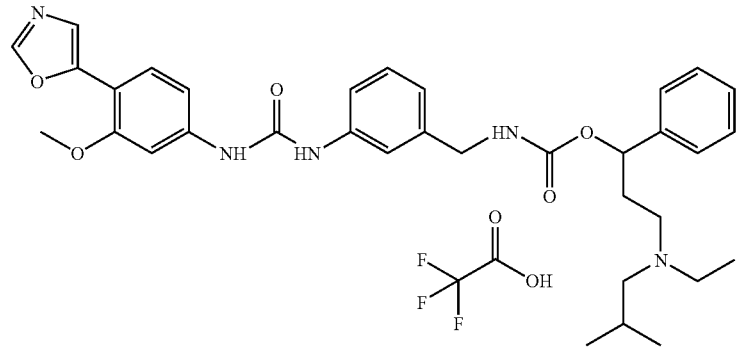
126 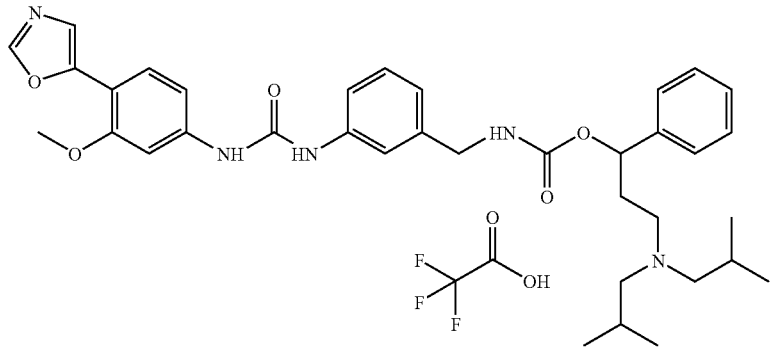

TABLE 1-continued
Compounds.
| 127 | 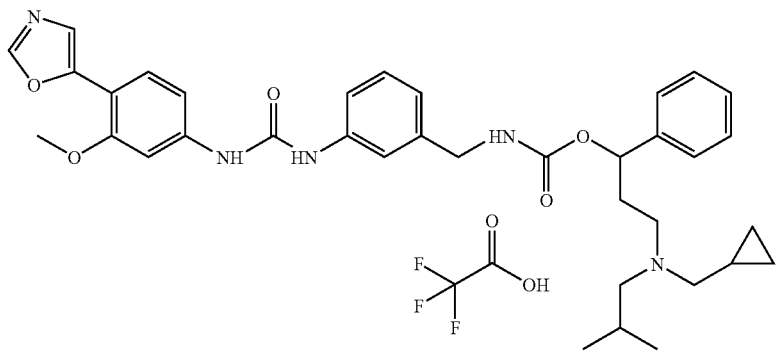 |
| 128 | 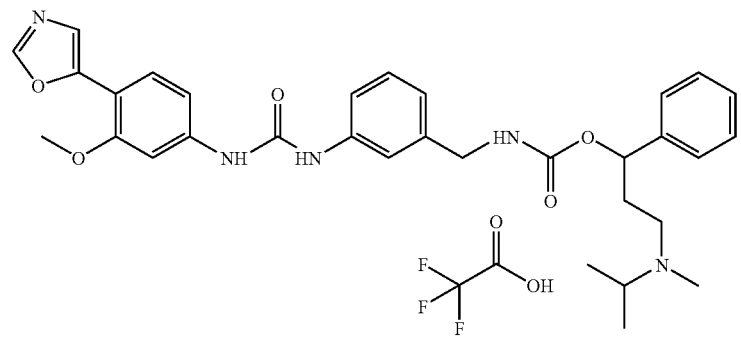 |
| 129 | 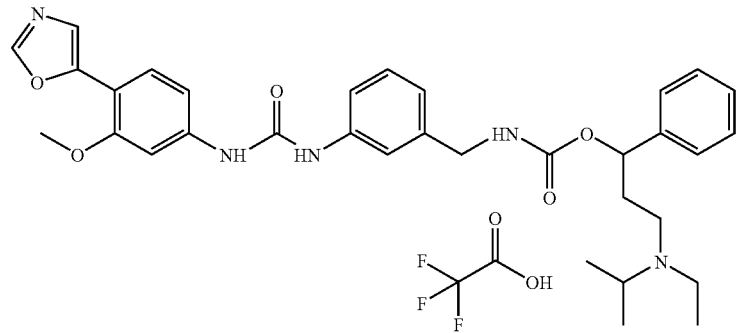 |
| 130 | 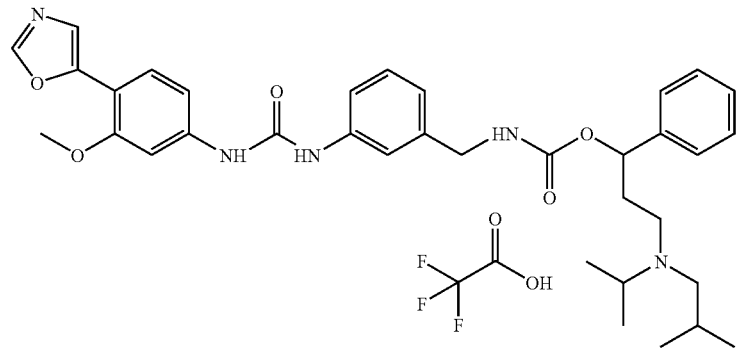 |

TABLE 1-continued
Compounds.
131 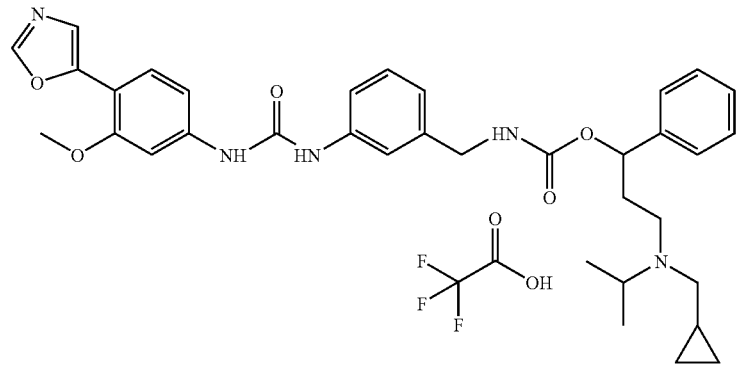
132 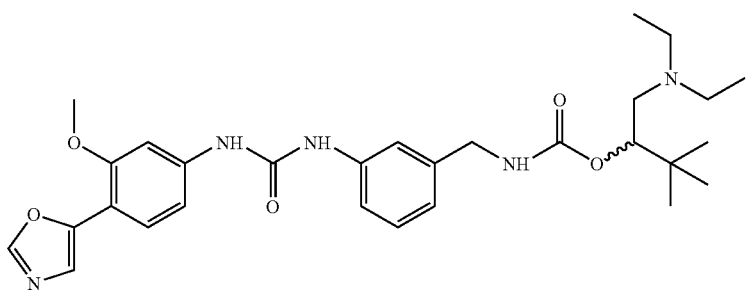
133 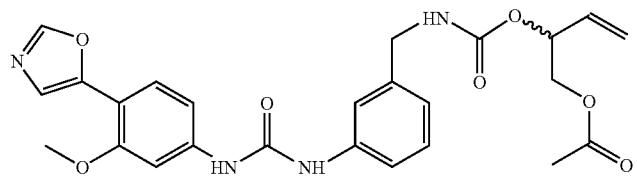
134 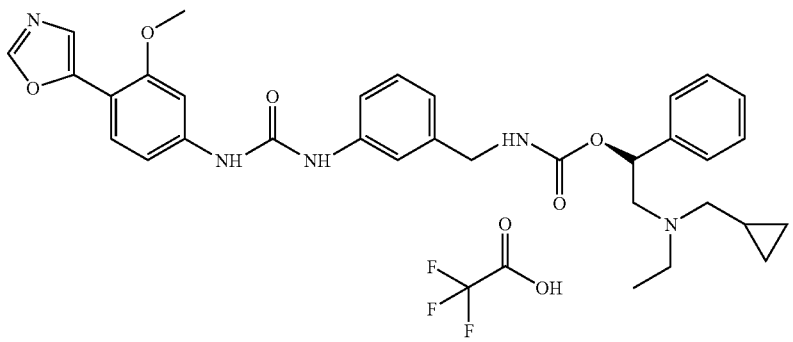
135 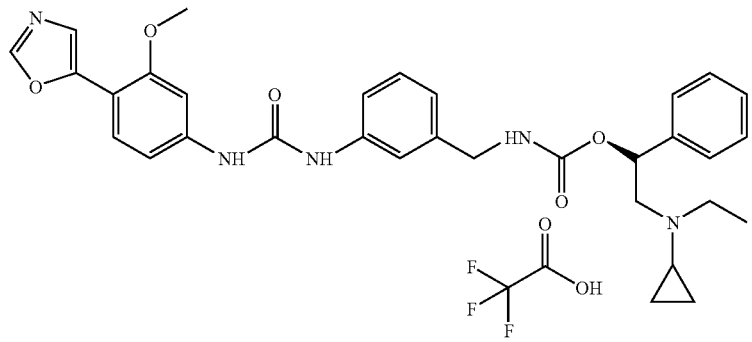

TABLE 1-continued
Compounds.
136 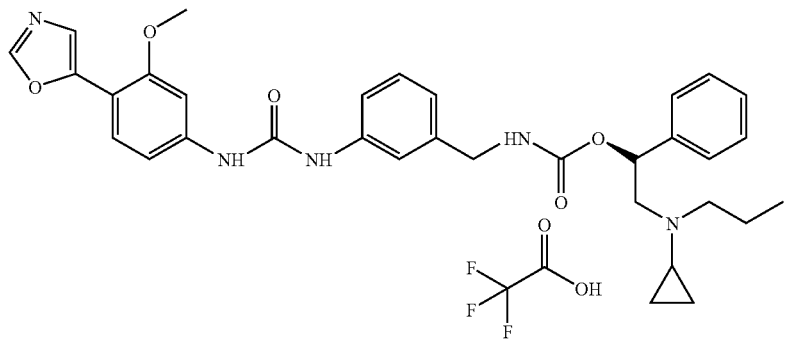
137 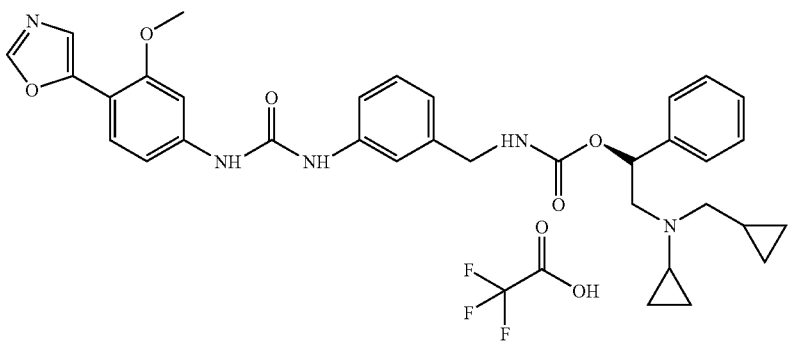
138 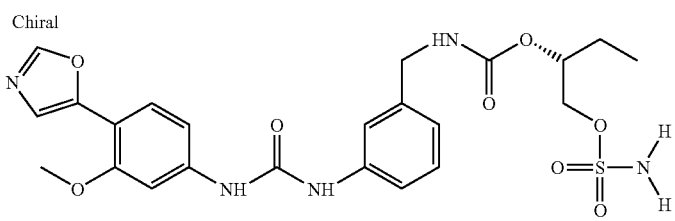
139 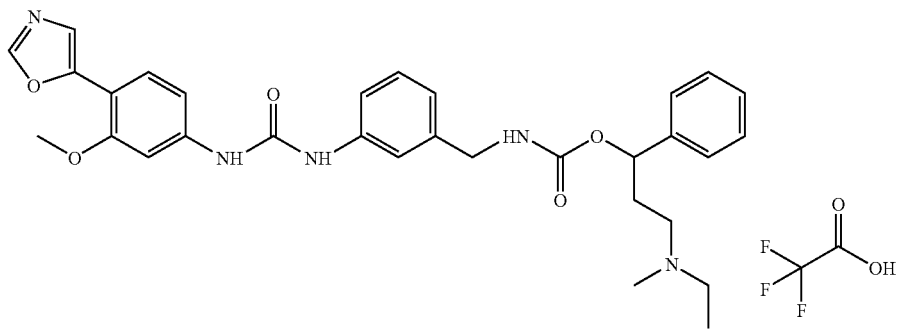
140 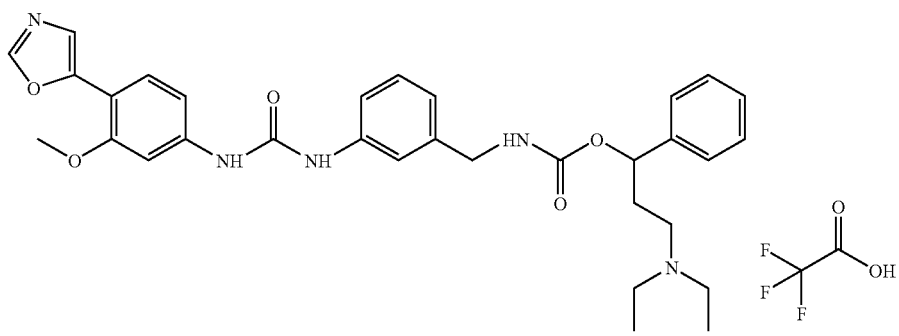

TABLE 1-continued
Compounds.
141 Chiral
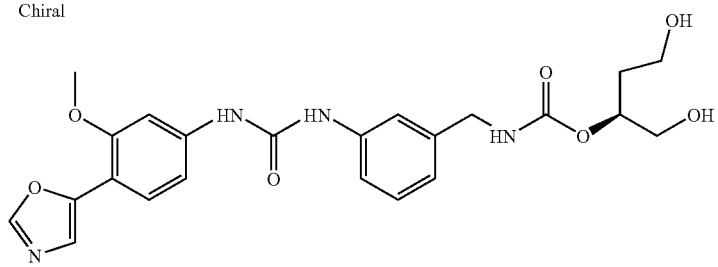
142
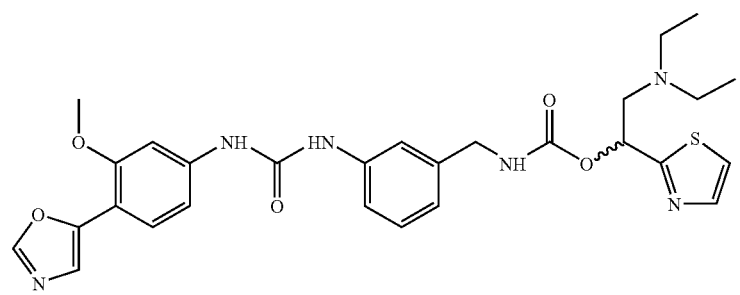
143
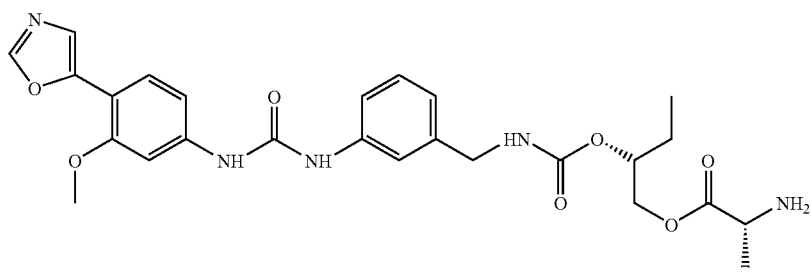
144
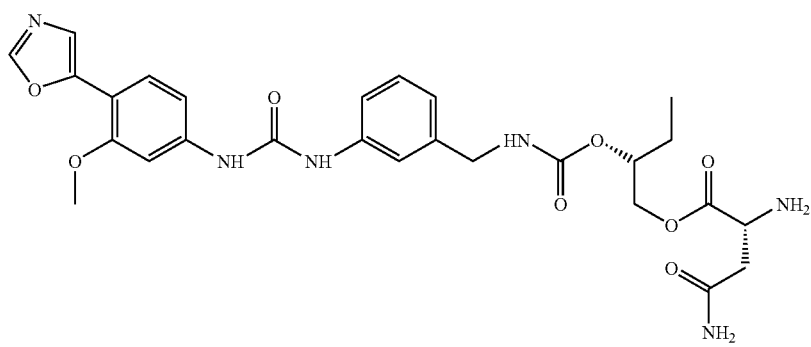
145
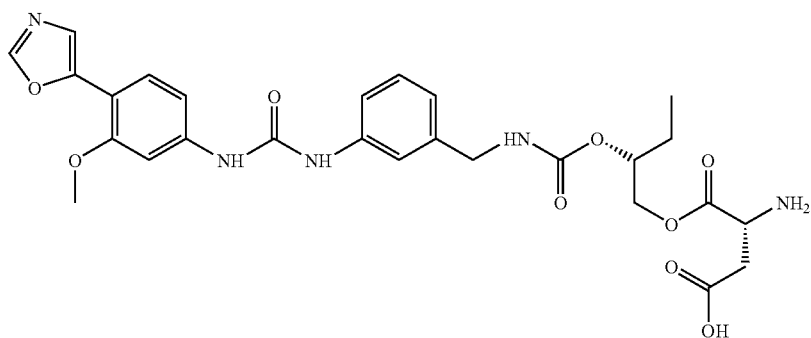

TABLE 1-continued
Compounds.
146
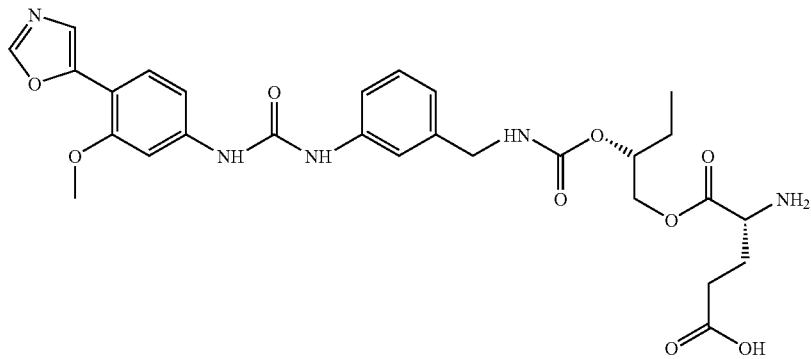
147
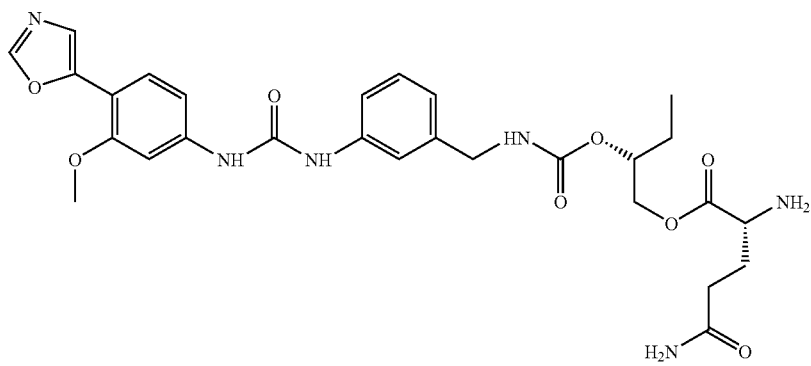
148
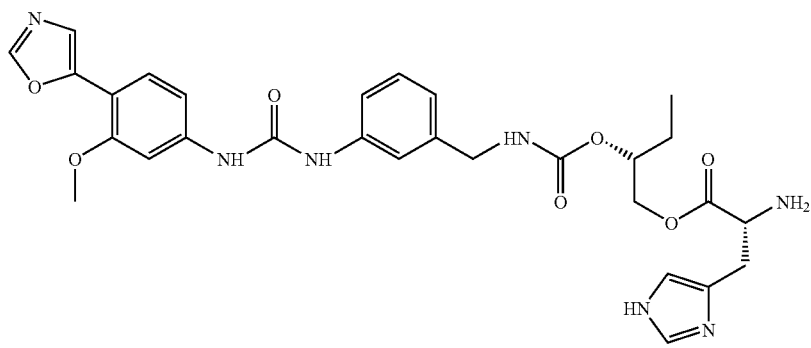
149
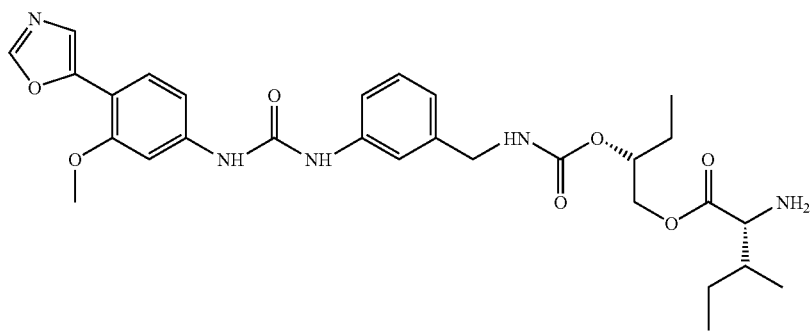

TABLE 1-continued
Compounds.
150 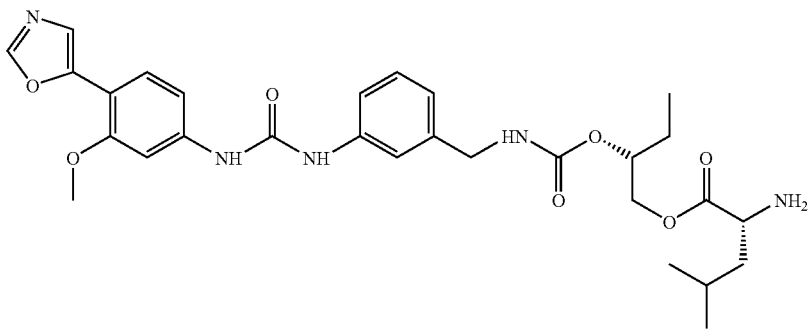
151 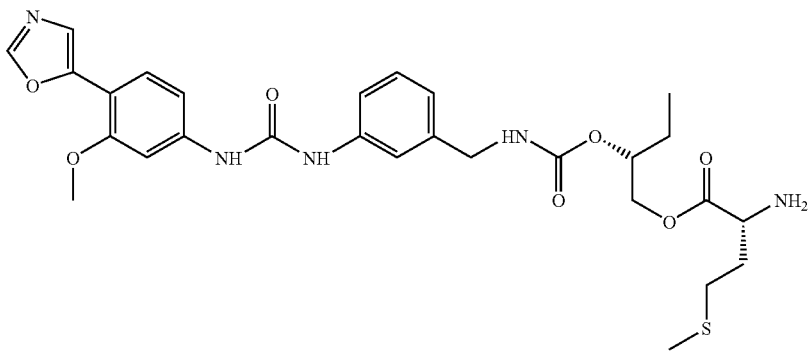
152 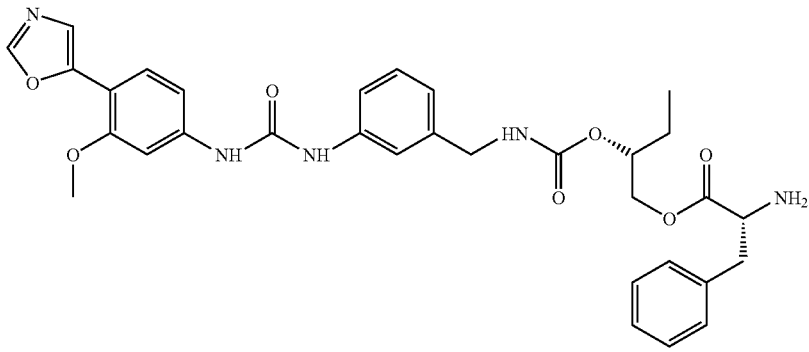
153 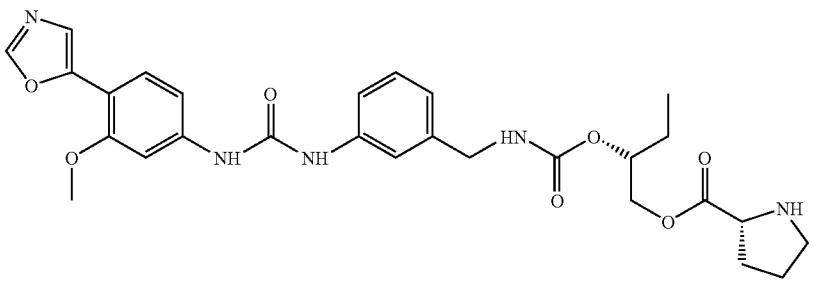

TABLE 1-continued
Compounds.
154 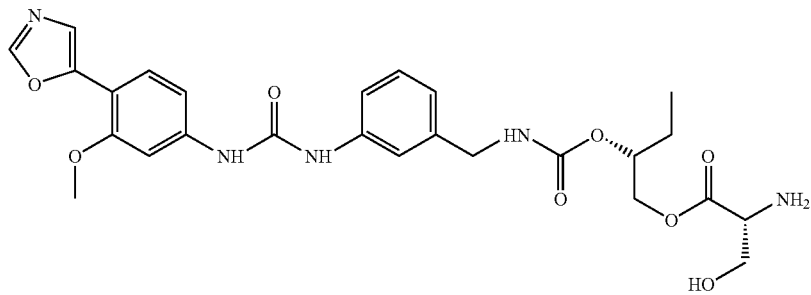
155 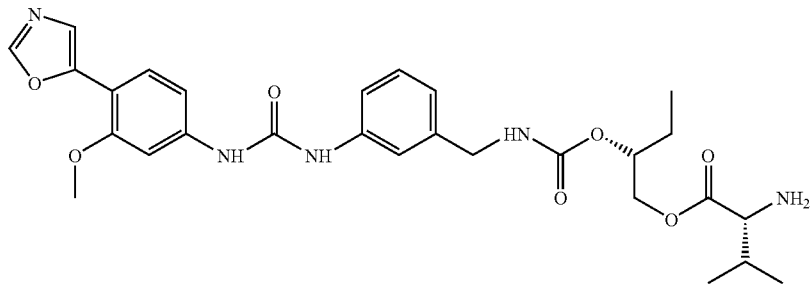
156 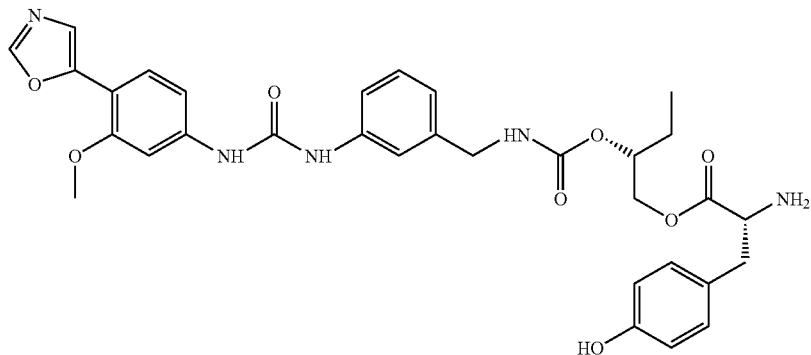
157 Chiral
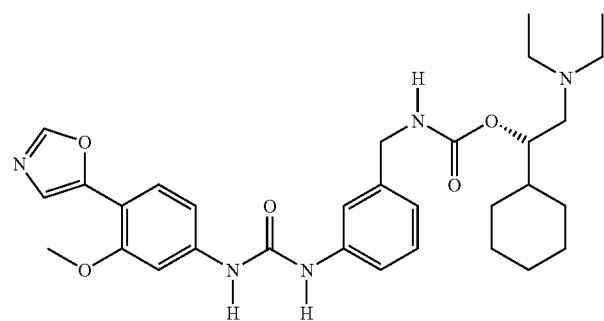

TABLE 1-continued
Compounds.
158 Chiral
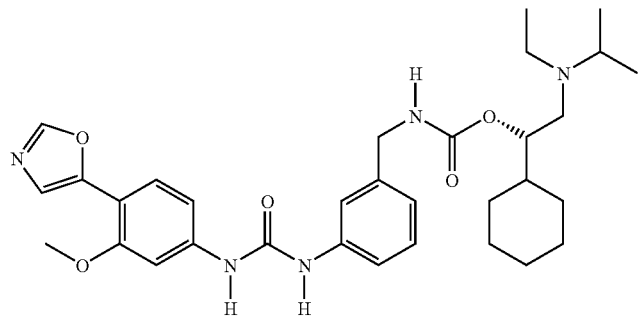
159 Chiral
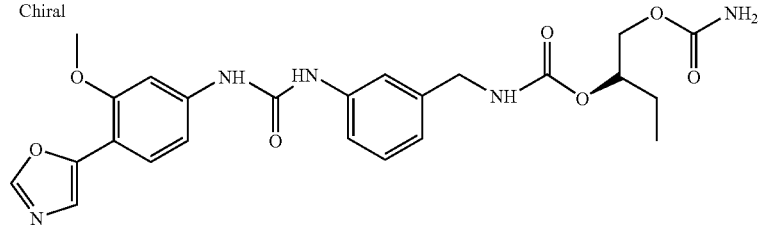
160
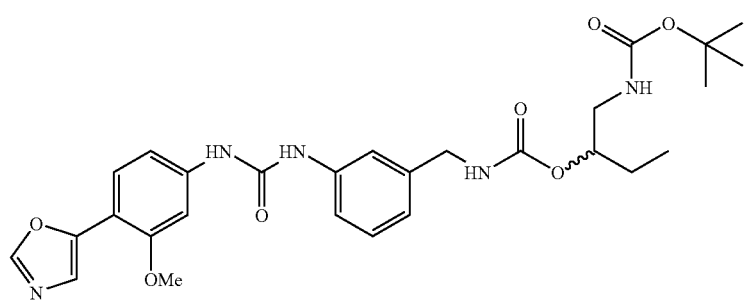
161
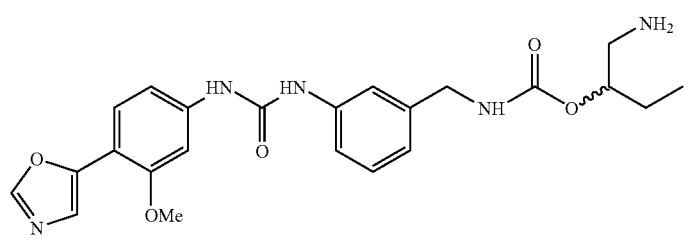
162 Chiral
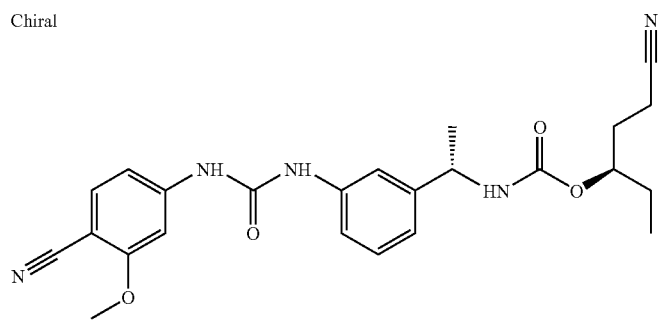

TABLE 1-continued

Compounds.

163

164

165

166 Chiral

167 Chiral

168 Chiral

TABLE 1-continued

Compounds.

| 169 | Chiral |
| 170 | Chiral |
| 171 | Chiral |
| 172 | Chiral |
| 173 | Chiral |
| 174 | Chiral |

TABLE 1-continued
Compounds.
175  Chiral
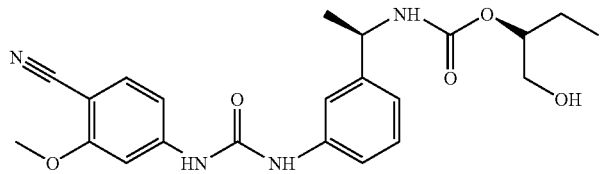
176  Chiral
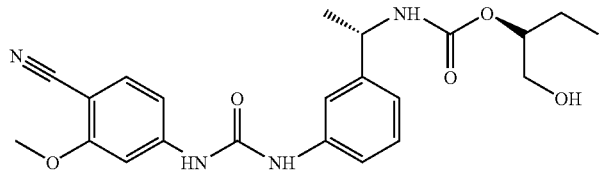
177
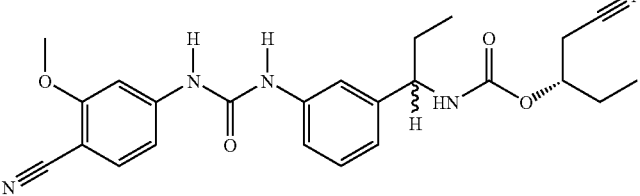
178
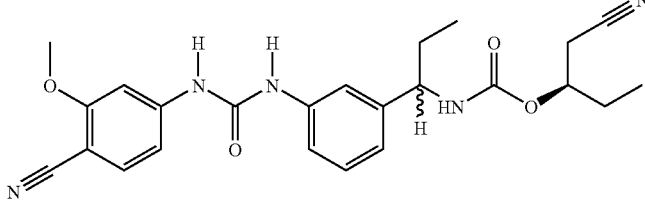
179  Chiral
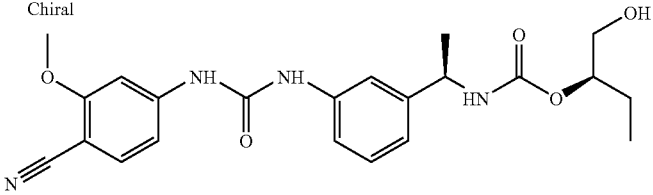
180  Chiral
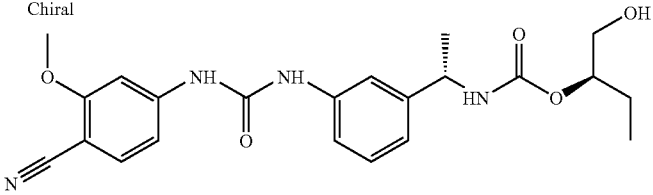
181  Chiral
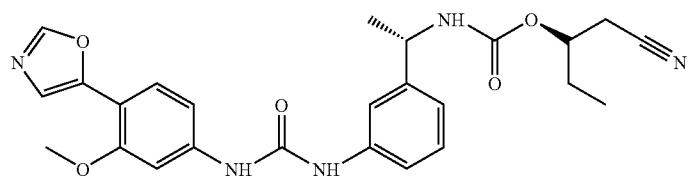

TABLE 1-continued

Compounds.

| 182 | [structure] |
| 183 | [structure] |
| 184 | Chiral [structure] |
| 185 | Chiral [structure] |
| 186 | [structure] |
| 187 | [structure] |

In the above table, certain compounds are shown as salts. It should be understood that the scope of the compounds set forth in any given entry in the table covers all forms of the depicted compound, not just the salt shown.

According to a more preferred embodiment, the present invention provides a composition comprising:
1. fludarabine;
2. compound No. 181; and
3. a pharmaceutically acceptable carrier.

According to a more preferred embodiment, the present invention provides a composition comprising:
1. fludarabine;
2. compound No. 169; and
3. a pharmaceutically acceptable carrier.

When stereochemistry is not specifically indicated, the compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention, unless otherwise indicated. Each stereogenic carbon may be of the R or S configuration.

Combinations of substituents and variables envisioned by this invention are only those that result in the formation of stable compounds. The term "stable", as used herein, refers to compounds that possess stability sufficient to allow manufacture and maintenance of the integrity for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds within the compositions of this invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those which increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of the compounds of this invention.

Pharmaceutically acceptable salts of the compounds within the compositions of this invention include those derived from pharmaceutically acceptable inorganic and organic acids and bases. Examples of suitable acid salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds within the compositions of this invention may be synthesized using conventional techniques. Advantageously, these compounds are conveniently synthesized from readily available starting materials. The synthetic routes to these compounds, and the syntheses of the specific compounds within Table 1 are disclosed in International PCT Application WO 00/56331, which publication is incorporated herein by reference.

The compounds within the compositions of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of this invention.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, Ph. Helv., or a similar alcohol, or carboxymethyl cellulose or similar dispersing agents which are commonly used in the formulation of pharmaceutically acceptable dosage forms such as emulsions and or suspensions Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions and/or emulsions are administered orally, the active ingredient may be suspended or dissolved in an oily phase and combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day each of fludarabine and the IMPDH inhibitory compound described herein are useful in a monotherapy and/or in combination therapy for the prevention and treatment of IMPDH-mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In the compositions of the present invention both, the IMPDH inhibitor and fludarabine, should be present at dosage levels of between about 10 to 100%, and more preferably between about 10 to 80% of the dosage normally administered in a monotherapy regimen. Fludarabine may be administered separately, as part of a multiple dose regimen, from the IMPDH inhibitory compounds. Alternatively, Fludarabine may be part of a single dosage form, mixed together with the compounds of this invention in a single composition.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, the patient's disposition to the disease and the judgment of the treating physician.

In an alternate embodiment, this invention provides methods of treating an IMPDH-mediated disease in a mammal comprising the step of administrating to said mammal any of the pharmaceutical compositions described above. Such methods may comprise the additional step of administering to said mammal an agent selected from an anti-inflammatory agent, immunosuppressant, an anti-cancer agent, an anti-viral agent, or an anti-vascular hyperproliferation compound. Such additional agent may be administered to the mammal prior to, concurrently with, or following the administration of a composition of the present invention.

In a preferred embodiment, these methods are useful in suppressing an immune response in a mammal. Such methods are useful in treating or preventing diseases, including, transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

In another alternate preferred embodiment, these methods are useful for treating tumors and cancer in a mammal. Such methods are useful in treating or preventing diseases, including, liquid and solid tumors and malignancies, such as lymphoma, leukemia and related disorders, myelodysplastic syndrome, metastatic melanoma, and other forms of cancer, such as breast cancer, colon cancer, pancreatic cancer, and prostate cancer.

According to another embodiment, the compounds of the present invention and the compositions of the present invention are useful in treating breast cancer or myelomas, preferably, multiple myeloma. According to a more preferred embodiment, the present invention provides a method of treating multiple myeloma comprising the step of administering to a patient in need thereof compound no. 181 or compound no. 169, optionally combined with fludarabine. More preferably, said method of treating multiple myeloma comprises the step of administering to said patient compound no. 181. According to another more preferred embodiment, the present invention provides a method of treating breast cancer comprising the step of administering to a patient in need thereof compound no. 181 or compound no. 169, optionally combined with fludarabine. More preferably, said method of treating breast cancer comprises the step of administering to said patient compound no. 181.

These methods comprise the step of administering to the mammal a composition of this invention. In a preferred embodiment, this particular method comprises the additional step of administering to said mammal a composition of the present invention wherein said composition contains fluradabine or a derivative or analog thereof.

More preferred embodiments of the above methods are those that employ the preferred compositions as described above.

In order that this invention be more fully understood, the following examples are set forth. These examples are for the purpose of illustration only and are not to be construed as limiting the scope of the invention in any way.

Example 1

Apoptosis Assay

Purpose
To evaluate apoptosis of cell by measuring AnnexinV positive cells using the Guava Personal Cytometer technology in the presence or absence of compound 181.
Reagents
1. Medium: RPMI1640 (JRH #51501-79P) supplemented with 10% FBS (IRVINE Scientific, CA), 50 U/ml penicillin+50 ug/ml streptomycin (Gibco), 300 ug/ml L-glutamine (Gibco), 10 mM HEPES (Gibco); 4.5 g/L glucose.
2. Nexin Kit (Guava Catalog No. 4700-0010).
3. Guava Technologies Personal Cytometer.
4. Daudi cell line (ATCC).
5. 2-Fluoroadenine-9-b-D-arabinofuranoside (F-ara-A Fludarabine des-phosphate), Sigma catalog#F2773.
Procedure
Day 0:
1. Dilute cells to 2~2.5×10$^5$/ml in medium.
2. Plate 100 ul cell suspension in media in each well of a 96-well plate, 1 ml in each well of a 24-well plate or 1.2 ml in each well of a 12 well plate.
3. Prepare compound solutions in medium.
4. Add 100 μl of test drug solutions to each well of 96-well plate, or 1 ml to each well of 24-well plate. DMSO concentration is 0.1~0.2% for all wells.
5. Incubate plates (37° C., 5% $CO_2$).
Day 3:
1. Follow procedure provided by the manufacturer for staining cells with the Guava Nexin Kit.
2. Analyze samples with the Guava Personal Cytometer following manufacturer's directions.
3. Analyze results for synergy using Biosoft-CalcuSyn Program.

The combination of compound 181 and fludarabine results in a much greater % apoptosis due to the synergy therebetween.

The Combination Index Values for Compound No. 181 and Fludarabine (1:1) at ED50, ED 75, and ED90 were 0.21, 0.079, and 0.03, respectively, thus demonstrating strong synergistic effect.

While we have hereinbefore presented a number of embodiments of this invention, it is apparent that our basic construction can be altered to provide other embodiments that utilize the methods of this invention. Therefore, it will be appreciated that the scope of this invention is to be defined by the claims appended hereto rather than the specific embodiments that have been presented hereinbefore by way of example.

We claim:
1. A composition comprising:
(a) fludarabine;
(b) compound 181:

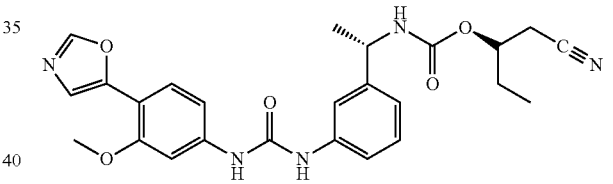

wherein each of said fludarabine and said compound 181 are independently present in a therapeutically effective amount; and
(c) a pharmaceutically acceptable carrier.
2. A method for treating lymphoma, leukemia, myelodysplastic syndrome, metastatic melanoma breast cancer, colon cancer, pancreatic cancer, and prostate cancer in a mammal comprising the step of administrating to said mammal a composition according to claim 1.

* * * * *